US012533456B2

(12) United States Patent
Kusters et al.

(10) Patent No.: US 12,533,456 B2
(45) Date of Patent: Jan. 27, 2026

(54) SYSTEMS AND METHODS FOR PROCESSING WHOLE BLOOD INTO RED BLOOD CELL, PLASMA, AND PLATELET PRODUCTS

(71) Applicant: Fenwal, Inc., Lake Zurich, IL (US)

(72) Inventors: Benjamin E. Kusters, Pleasant Prairie, WI (US); Richard I. Brown, Northbrook, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 797 days.

(21) Appl. No.: 17/848,821

(22) Filed: Jun. 24, 2022

(65) Prior Publication Data

US 2022/0409799 A1 Dec. 29, 2022

Related U.S. Application Data

(60) Provisional application No. 63/214,867, filed on Jun. 25, 2021.

(51) Int. Cl.
*A61M 1/36* (2006.01)
*A61M 1/38* (2006.01)
(Continued)

(52) U.S. Cl.
CPC ...... *A61M 1/3693* (2013.01); *A61M 1/36224* (2022.05); *A61M 1/362262* (2022.05);
(Continued)

(58) Field of Classification Search
CPC ............ A61M 1/3693; A61M 1/36224; A61M 1/362262; A61M 1/38; A61M 2202/0415;
(Continued)

(56) References Cited

U.S. PATENT DOCUMENTS 4,157,723 A 6/1979 Granzow et al.
4,753,697 A 6/1988 Shaposka et al.
(Continued)

FOREIGN PATENT DOCUMENTS

EP 0775010 A1 5/1997
EP 2476447 A1 7/2012
WO 2021194824 A1 9/2021

OTHER PUBLICATIONS

Extended European Search Report for European Application No. 22180869.4 Dated Nov. 14, 2022.

*Primary Examiner* — Duane Smith
*Assistant Examiner* — Shuyi S. Liu
(74) *Attorney, Agent, or Firm* — Cook Alex Ltd.

(57) ABSTRACT

A processing device includes a pump system, a valve system, a centrifuge, and a controller. A fluid flow circuit is mounted to the device to execute a procedure in which whole blood is processed into a red blood cell product, a plasma product, and a platelet concentrate product. The blood is first separated into red blood cells, buffy coat, and plasma using the centrifuge, with the red blood cells and plasma being removed from the centrifuge, while the buffy coat remains in the centrifuge. The fluid remaining in the centrifuge is circulated through the centrifuge to form a homogenous mixture. Once the mixture is formed, it is separated in the centrifuge into platelet concentrate and red blood cells. A platelet product is then collected by using whole blood or previously collected red blood cells to push the platelet concentrate from the centrifuge to a collection container.

22 Claims, 17 Drawing Sheets

(51) Int. Cl.
*B01D 36/04* (2006.01)
*B04B 5/04* (2006.01)
*B04B 11/02* (2006.01)

(52) U.S. Cl.
CPC ............. *A61M 1/38* (2013.01); *B01D 36/045* (2013.01); *B04B 5/0442* (2013.01); *B04B 11/02* (2013.01); *A61M 2202/0415* (2013.01); *A61M 2202/0427* (2013.01); *A61M 2202/0429* (2013.01); *A61M 2202/0439* (2013.01); *A61M 2205/3306* (2013.01); *A61M 2205/3331* (2013.01); *A61M 2205/3393* (2013.01)

(58) Field of Classification Search
CPC .. A61M 2202/0427; A61M 2202/0429; A61M 2202/0439; A61M 2205/3306; A61M 2205/3331; A61M 2205/3393; A61M 1/0272; A61M 1/0281; A61M 1/0209; B01D 36/045; B04B 5/0442; B04B 11/02
USPC .............................. 494/37, 43; 210/782, 194
See application file for complete search history.

(56) References Cited

U.S. PATENT DOCUMENTS

| | | | |
|---|---|---|---|
| 5,156,701 | A | 10/1992 | Spencer et al. |
| 5,158,630 | A | 10/1992 | Shaposka et al. |
| 6,849,039 | B2 | 2/2005 | Min et al. |
| 6,899,666 | B2 | 5/2005 | Brown |
| 8,075,468 | B2 | 12/2011 | Min et al. |
| 9,440,396 | B2 | 9/2016 | Kusters et al. |
| 10,040,247 | B2 | 8/2018 | Schwalm et al. |
| 10,307,582 | B2 | 6/2019 | Wegener et al. |
| 2008/0087614 | A1 | 4/2008 | Min et al. |
| 2009/0215602 | A1 | 8/2009 | Min et al. |
| 2018/0078582 | A1 | 3/2018 | Min et al. |
| 2019/0201916 | A1 | 7/2019 | Min et al. |

SYSTEMS AND METHODS FOR PROCESSING WHOLE BLOOD INTO RED BLOOD CELL, PLASMA, AND PLATELET PRODUCTS

CROSS-REFERENCE TO RELATED APPLICATIONS

This application claims the benefit of and priority of U.S. Provisional Patent Application Ser. No. 63/214,867, filed Jun. 25, 2021, the contents of which are incorporated by reference herein.

BACKGROUND

Field of the Disclosure

The present disclosure relates to separation of whole blood. More particularly, the present disclosure relates to separation of whole blood into red blood cell, plasma, and platelet products.

Description of Related Art

It is well known to collect whole blood from donors using manual collection procedures through blood drives, donor visits to blood centers or hospitals and the like. In such procedures, blood is typically collected by simply flowing it from the donor under the force of gravity and venous pressure into a collection container (e.g., a flexible pouch or bag). Although various blood collection instruments may be used to aid or expedite the collection of blood or blood components.

The collection container in manual collection is often part of a larger pre-assembled arrangement of tubing and containers (sometimes called satellite containers) that are used in further processing of the collected whole blood. More specifically, the whole blood is typically first collected in what is called a primary collection container that also contains an anticoagulant, such as but not limited to a solution of sodium citrate, phosphate, and dextrose ("CPD").

After initial collection, it is a common practice to transport the collected whole blood to another facility or location, sometimes called a "back lab," for further processing to separate red blood cells, platelet, and plasma from the whole blood, which may include carrying out additional processes, such as cell washing and plasma cryoprecipitate production and collection. This processing usually entails manually loading the primary collection container and associated tubing and satellite containers into a centrifuge to separate the whole blood into concentrated red cells and platelet-rich or platelet-poor plasma. The separated components may then be expressed from the primary collection container into one or more of the satellite containers, with the red blood cells being combined with an additive or preservative solution pre-filled in one of the satellite containers. After the above steps, the blood components may be again centrifuged, if desired, for example to separate platelets from plasma. The overall process requires multiple large floor centrifuges and fluid expression devices. Because of the multiple operator interactions, the process is labor intensive, time consuming, and subject to human error.

Thus, there have been continuing efforts to automate the apparatus and systems used in the post-collection processing of whole blood, and recently it has been proposed to employ an automated blood component separator for such post-collection processing. The subject matter disclosed herein provides further advances in various aspects of the apparatus, systems, and methods that may be employed in post-collection processing systems (while also being applicable to processing of blood being drawn from a living donor) by using continuous flow centrifugation to separate a unit of whole blood into red blood cell, plasma, and platelet products.

Unlike previous processes (in which multiple buffy coats are harvested, pooled, and then separated to produce a platelet product), the current method and system resuspend the platelets of a single buffy coat in plasma and harvest a platelet product. The platelet product can be easily pooled with similarly obtained platelet products without the need for subsequent processing and potential loss of platelets, as is the case of conventional buffy coat harvesting and pooling. Without the subsequent processing (and possible platelet loss), it may be possible to obtain the desired amount of platelet product using fewer units of blood than are required by the conventional approach.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood processing system includes a reusable processing device and a disposable fluid flow circuit. The processing device includes a pump system, a valve system, a centrifuge, and a controller, while the disposable fluid flow circuit includes a processing chamber received by the centrifuge, a red blood cell collection container, a platelet concentrate collection container, and a plurality of conduits fluidly connecting the components of the fluid flow circuit. The controller is configured to command the pump system and the valve system to cooperate to convey whole blood from a blood source to the processing chamber. The controller is also configured to execute an establish separation stage in which the centrifuge operates to separate the whole blood in the processing chamber into plasma and red blood cells and the pump system and the valve system cooperate to convey separated plasma and red blood cells out of the processing chamber, recombine the separated plasma and red blood cells as recombined whole blood, and convey the recombined whole blood into the processing chamber. The controller is further configured to execute a collection stage in which the pump system conveys the whole blood from the blood source to the processing chamber; the centrifuge separates the whole blood in the processing chamber into plasma, a buffy coat, and red blood cells; and the pump system and the valve system cooperate to convey at least a portion of the separated plasma out of the processing chamber and to convey at least a portion of the separated red blood cells out of the processing chamber and into the red blood cell collection container, with a fluid including the buffy coat remaining in the processing chamber. Next, the controller executes a platelet resuspension stage comprising a first phase in which the centrifuge is deactivated and the pump system and the valve system cooperate to circulate the fluid in the processing chamber through the fluid flow circuit to form a homogenous mixture, and a second phase in which the centrifuge operates to separate the homogenous mixture into a platelet concentrate and red blood cells. The controller then executes a platelet harvest stage in which the pump system and the valve system cooperate to convey whole blood from the blood source or at least a portion of the contents of the red blood cell collection container into the processing chamber to convey at least a portion of the platelet concentrate out of the processing chamber and into the platelet concentrate collection container.

In another aspect, a method is provided for processing whole blood into a red blood cell product, a plasma product, and a platelet product. The method includes conveying whole blood from a blood source to a processing chamber of a fluid flow circuit. Next, an establish separation stage is executed in which a centrifuge is operated to separate the whole blood in the processing chamber into plasma and red blood cells, separated plasma and red blood cells are conveyed out of the processing chamber and recombined as recombined whole blood, and the recombined whole blood is conveyed into the processing chamber. After the establish separation stage, a collection stage is executed. During the collection stage, whole blood is conveyed from the blood source to the processing chamber and the centrifuge is operated to separate the whole blood in the processing chamber into plasma, a buffy coat, and red blood cells. At least a portion of the separated plasma is conveyed out of the processing chamber and at least a portion of the separated red blood cells is conveyed out of the processing chamber and into a red blood cell collection container of the fluid flow circuit, with a fluid including the buffy coat remaining in the processing chamber during the collection stage. Next, a platelet resuspension stage is executed that includes a first phase in which the centrifuge is deactivated and the fluid in the processing chamber is recirculated through the fluid flow circuit to form a homogenous mixture and a second phase in which the centrifuge is operated to separate the homogenous mixture into a platelet concentrate and red blood cells. Finally, a platelet harvest stage is executed in which whole blood from the blood source or at least a portion of the contents of the red blood cell collection container is conveyed into the processing chamber to convey at least a portion of the platelet concentrate out of the processing chamber and into a platelet concentrate collection container of the fluid flow circuit.

In yet another aspect, a blood processing device includes a pump system, a valve system, a centrifuge, and a controller. The controller is configured to command the pump system and the valve system to cooperate to convey whole blood from a blood source into the centrifuge. The controller is also configured to execute an establish separation stage in which the centrifuge operates to separate the whole blood in the centrifuge into plasma and red blood cells and the pump system and the valve system cooperate to convey separated plasma and red blood cells out of the centrifuge, recombine the separated plasma and red blood cells as recombined whole blood, and convey the recombined whole blood into the centrifuge. The controller is further configured to execute a collection stage in which the pump system conveys the whole blood from the blood source to the centrifuge, the centrifuge separates the whole blood in the centrifuge into plasma, a buffy coat, and red blood cells, and the pump system and the valve system cooperate to convey at least a portion of the separated plasma out of the centrifuge and to convey at least a portion of the separated red blood cells out of the centrifuge for collection, with a fluid including the buffy coat remaining in the centrifuge. Next, the controller executes a platelet resuspension stage comprising a first phase in which the centrifuge is deactivated and the pump system and the valve system cooperate to circulate the fluid in the centrifuge through the centrifuge to form a homogenous mixture, and a second phase in which the centrifuge operates to separate the homogenous mixture into a platelet concentrate and red blood cells. The controller then executes a platelet harvest stage in which the pump system and the valve system cooperate to convey whole blood from the blood source or at least a portion of the collected red blood cells into the centrifuge to convey at least a portion of the platelet concentrate out of the centrifuge for collection.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
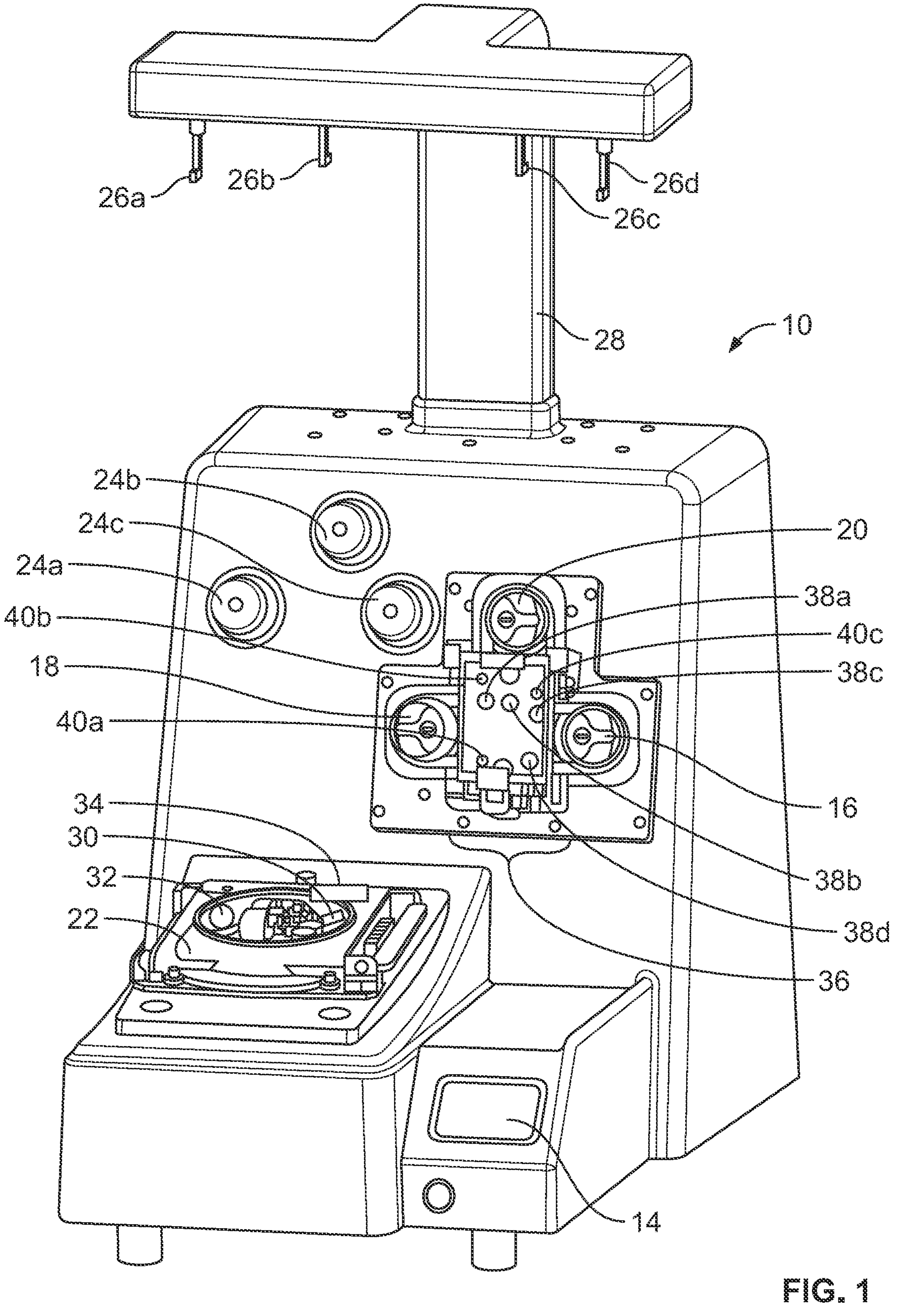
FIG. 1 is a perspective view of an exemplary reusable hardware component of a blood processing system which is configured to receive a disposable fluid flow circuit.
Figure 2:
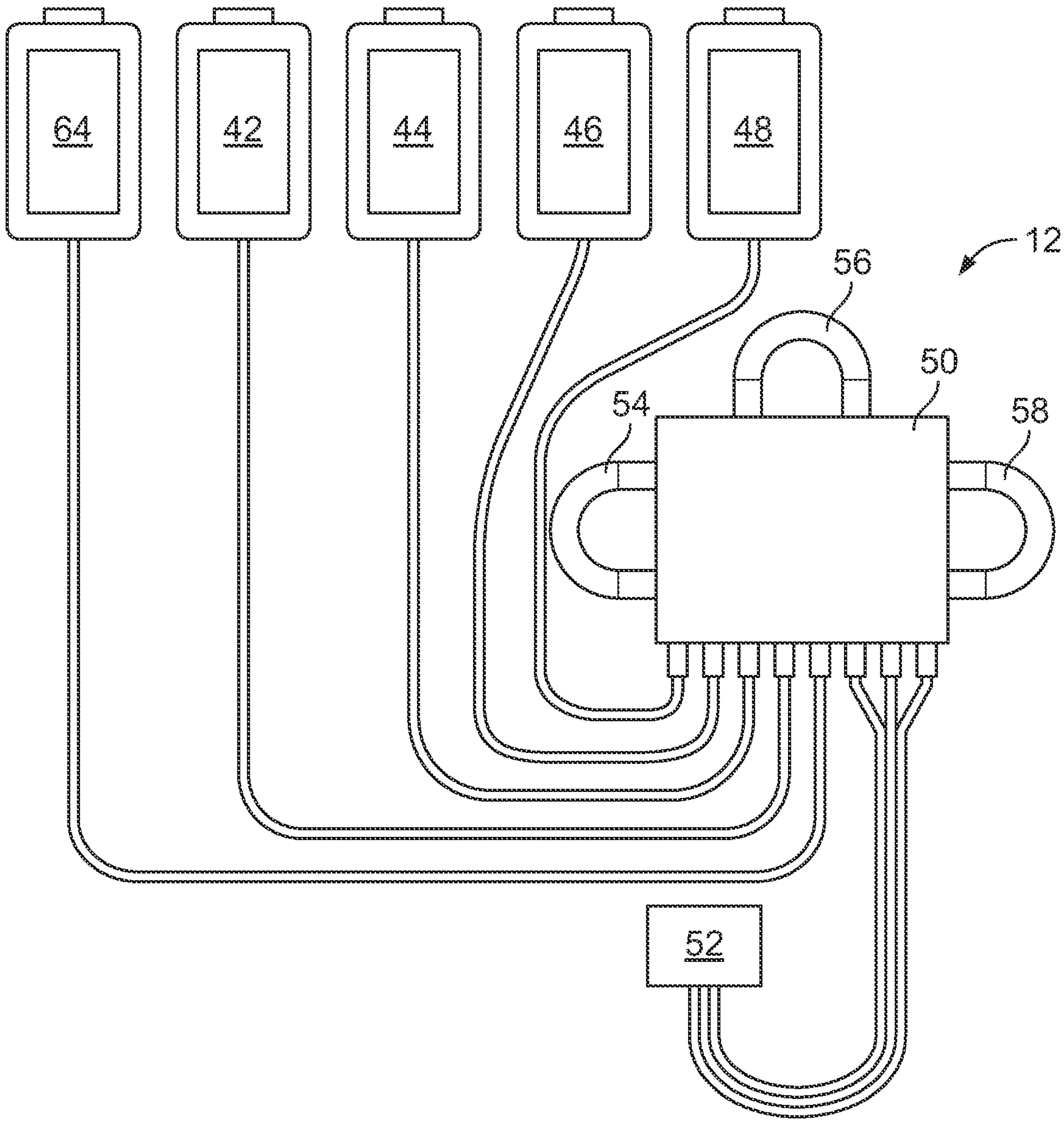
FIG. 2 is a plan view of an exemplary disposable fluid flow circuit for use in combination with the durable hardware component of FIG. 1.

FIG. 1 depicts a reusable hardware component or processing device of a blood processing system, generally designated 10, while FIG. 2 depicts a disposable fluid flow circuit, generally designated 12, to be used in combination with the processing device 10 for processing collected whole blood. The illustrated processing device 10 includes associated pumps, valves, sensors, displays, and other apparatus for configuring and controlling flow of fluid through the fluid flow circuit 12, described in greater detail below. The blood processing system may be directed by a controller integral with the processing device 10 that includes a programmable microprocessor to automatically control the operation of the pumps, valves, sensors, etc. The processing device 10 may also include wireless communication capabilities to enable the transfer of data from the processing device 10 to the quality management systems of the operator.

More specifically, the illustrated processing device 10 includes a user input and output touchscreen 14, a pump station including a first pump 16 (for pumping, e.g., whole blood), a second pump 18 (for pumping, e.g., plasma) and a third pump 20 (for pumping, e.g., additive solution), a centrifuge mounting station and drive unit 22 (which may be referred to herein as a "centrifuge"), and clamps 24*a-c*. The touchscreen 14 enables user interaction with the processing device 10, as well as the monitoring of procedure parameters, such as flow rates, container weights, pressures, etc. The pumps 16, 18, and 20 (collectively referred to herein as being part of a "pump system" of the processing device 10) are illustrated as peristaltic pumps capable of receiving tubing or conduits and moving fluid at various rates through the associated conduit dependent upon the procedure being performed. An exemplary centrifuge mounting station/drive unit is seen in U.S. Pat. No. 8,075,468 (with reference to FIGS. 26-28), which is hereby incorporated herein by reference. The clamps 24*a-c* (collectively referred to herein as being part of the "valve system" of the processing device 10) are capable of opening and closing fluid paths through the tubing or conduits and may incorporate RF sealers in order to complete a heat seal of the tubing or conduit placed in the clamp to seal the tubing or conduit leading to a product container upon completion of a procedure.

Sterile connection/docking devices may also be incorporated into one or more of the clamps 24*a-c*. The sterile connection devices may employ any of several different operating principles. For example, known sterile connection devices and systems include radiant energy systems that melt facing membranes of fluid flow conduits, as in U.S. Pat. No. 4,157,723; heated wafer systems that employ wafers for cutting and heat bonding or splicing tubing segments together while the ends remain molten or semi-molten, such as in U.S. Pat. Nos. 4,753,697; 5,158,630; and 5,156,701; and systems employing removable closure films or webs sealed to the ends of tubing segments as described, for example, in U.S. Pat. No. 10,307,582. Alternatively, sterile connections may be formed by compressing or pinching a sealed tubing segment, heating and severing the sealed end, and joining the tubing to a similarly treated tubing segment as in, for example, U.S. Pat. Nos. 10,040,247 and 9,440,396. All of the above-identified patents are incorporated by reference in their entirety. Sterile connection devices based on other operating principles may also be employed without departing from the scope of the present disclosure.

The processing device 10 also includes hangers 26*a-d* (which may each be associated with a weight scale) for suspending the various containers of the disposable fluid circuit 12. The hangers 26*a-d* are preferably mounted to a support 28, which is vertically translatable to improve the transportability of the processing device 10. An optical system comprising a laser 30 and a photodetector 32 is associated with the centrifuge 22 for determining and controlling the location of an interface between separated blood components within the centrifuge 22. An exemplary optical system is shown in U.S. Patent Application Publication No. 2019/0201916, which is hereby incorporated herein by reference. An optical sensor 34 is also provided to optically monitor one or more conduits leading into or out of the centrifuge 22.

The face of the processing device 10 includes a nesting module 36 for seating a flow control cassette 50 (FIG. 2) of the fluid flow circuit 12 (described in greater detail below). The cassette nesting module 36 is configured to receive various disposable cassette designs so that the system may be used to perform different types of procedures. Embedded within the illustrated cassette nesting module 36 are four valves 38*a-d* (collectively referred to herein as being part of the "valve system" of the processing device 10) for opening and closing fluid flow paths within the flow control cassette 50, and three pressure sensors 40*a-c* capable of measuring the pressure at various locations of the fluid flow circuit 12.

With reference to FIG. 2, the illustrated fluid flow circuit 12 includes a plurality of containers 42, 44, 46, 48, and 64 with a flow control cassette 50 and a processing/separation chamber 52 that is configured to be received in the centrifuge 22, all of which are interconnected by conduits or tubing segments, so as to permit continuous flow centrifugation. The flow control cassette 50 routes the fluid flow through three tubing loops 54, 56, 58, with each loop being positioned to engage a particular one of the pumps 16, 18, 20. The conduits or tubing may extend through the cassette 50, or the cassette 50 may have pre-formed fluid flow paths that direct the fluid flow.

In the fluid flow circuit 12 shown in FIG. 2, container 42 may be pre-filled with additive solution, container 44 may be filled with whole blood and connected to the fluid flow circuit 12 at the time of use, container 46 may be an empty container for the receipt of red blood cells separated from the whole blood, container 48 may be an empty container for the receipt of plasma separated from the whole blood, and container 64 may be an empty container for the receipt of platelet concentrate separated from the whole blood. While FIG. 2 shows a whole blood container 44 (configured as a blood pack unit, for example) as a blood source, it is within the scope of the present disclosure for the blood source to be a living donor, as will be described in greater detail herein.

The fluid flow circuit may optionally include an air trap 60 (FIG. 3) through which the whole blood is flowed prior to entering the separation chamber and/or a leukoreduction filter 62 through which the red blood cells are flowed prior to entering the red blood cell collection container 46.

The processing chamber 52 may be pre-formed in a desired shape and configuration by injection molding from a rigid plastic material, as shown and described in U.S. Pat. No. 6,849,039, which is hereby incorporated herein by reference. The specific geometry of the processing chamber 52 may vary depending on the elements to be separated, and the present disclosure is not limited to the use of any specific chamber design. For example, it is within the scope of the present disclosure for the processing chamber 52 to be configured formed of a generally flexible material, rather than a generally rigid material. When the processing chamber 52 is formed of a generally flexible material, it relies upon the centrifuge 22 to define a shape of the processing chamber 52. An exemplary processing chamber formed of a flexible material and an associated centrifuge are described in U.S. Pat. No. 6,899,666, which is hereby incorporated herein by reference.

In keeping with the disclosure, the controller of the processing device 10 is pre-programmed to automatically operate the system to perform one or more standard blood processing procedures selected by an operator by input to the touchscreen 14, and configured to be further programmed by the operator to perform additional blood processing procedures. The controller may be pre-programmed to substantially automate a wide variety of procedures, including, but not limited to: red blood cell and plasma production from a single unit of whole blood (as described in PCT patent application serial no. PCT/US21/22750), buffy coat pooling and separation into a platelet product (as described in U.S. Patent Application Publication No. 2018/0078582, which is hereby incorporated herein by reference), and platelet harvesting (as will be described in greater detail herein). The controller may also perform post-processing stages.

The pre-programmed blood processing procedures operate the system at pre-set settings for flow rates and centrifugation forces, and the programmable controller may be further configured to receive input from the operator as to one or more of flow rates and centrifugation forces for the standard blood processing procedure to override the pre-programmed settings.

In addition, the programmable controller is configured to receive input from the operator through the touchscreen 14 for operating the system to perform a non-standard blood processing procedure. More particularly, the programmable controller may be configured to receive input for settings for the non-standard blood processing procedure, including flow rates and centrifugation forces.

Figure 3:
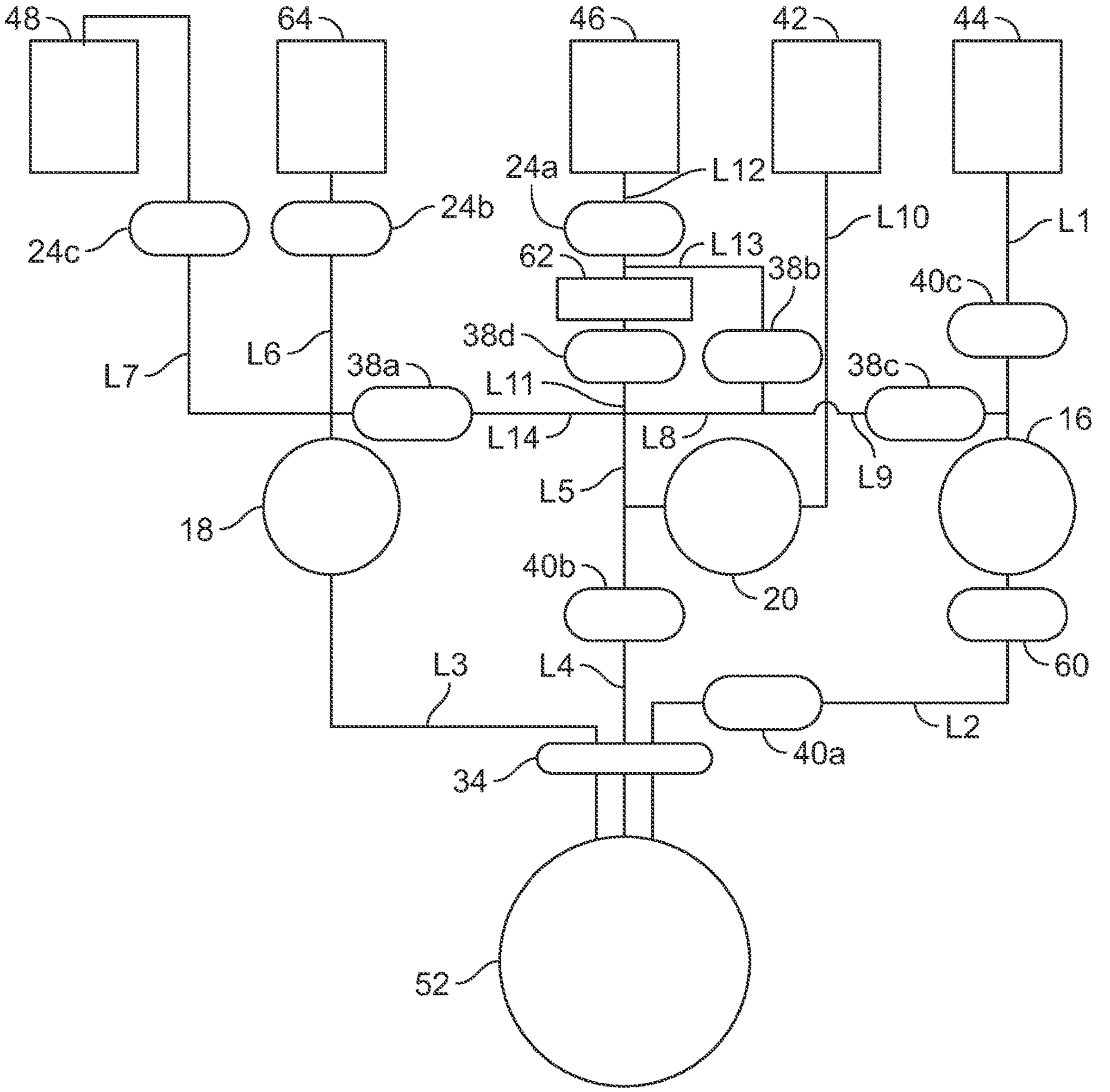
FIG. 3 is a schematic view of the fluid flow circuit of FIG. 2 mounted to the processing device of FIG. 1 to complete a blood processing system according to an aspect of the present disclosure.

In an exemplary procedure, the processing device 10 and the fluid flow circuit 12 may be used in combination to process whole blood into a red blood cell product, a plasma product, and a platelet product. The amount of whole blood to be processed may vary, with a single unit of blood being processed in one embodiment. FIG. 3 is a schematic illustration of the fluid flow circuit 12 mounted to the processing device 10, with selected components of the fluid flow circuit 12 and selected components of the processing device 10 being shown. FIGS. 4-17 show different stages of an exemplary procedure.

Figure 4:
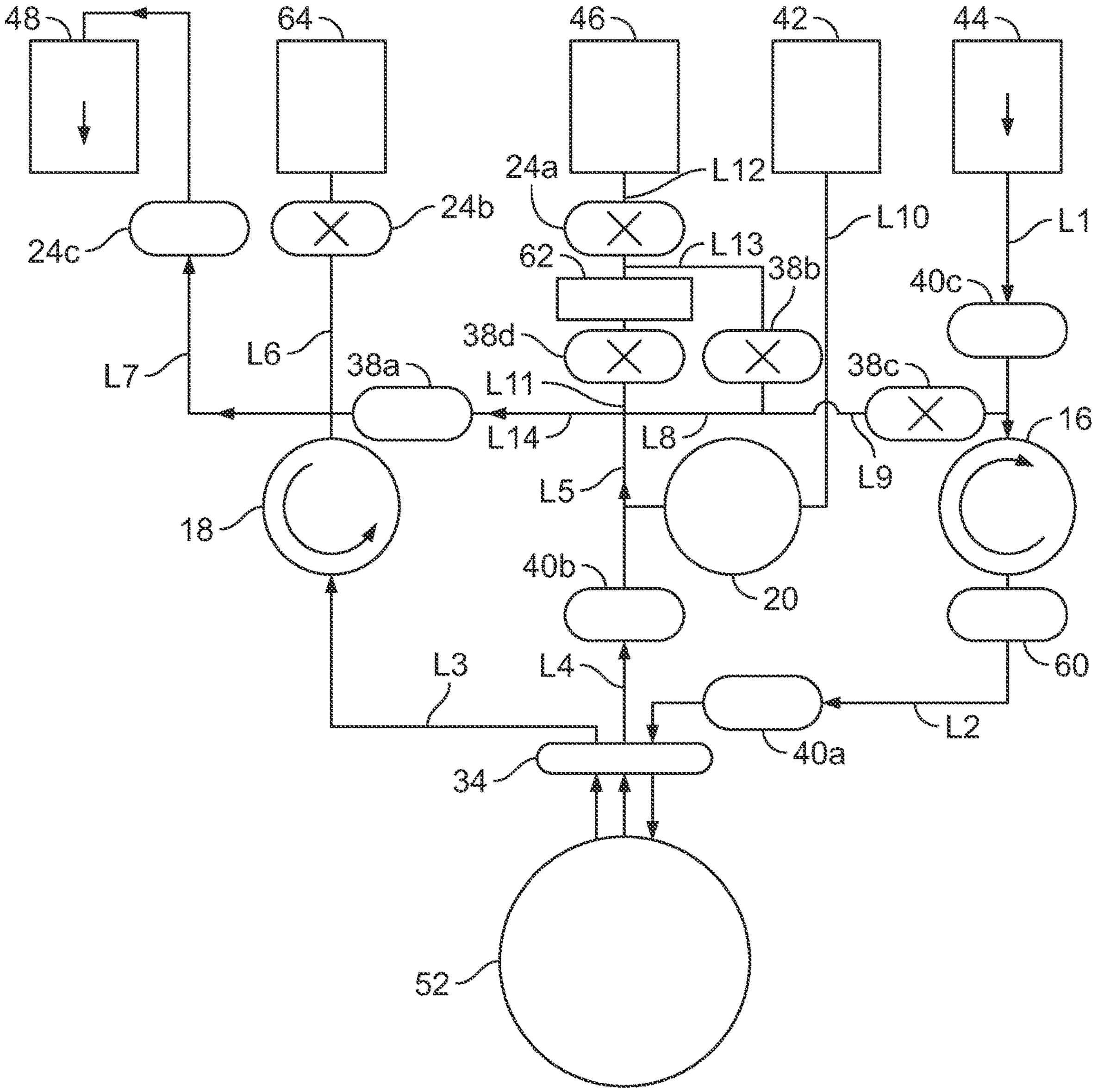
FIG. 4 is a schematic view of the blood processing system of FIG. 3 executing a “blood prime” stage of an exemplary blood processing procedure.

In an initial stage, which is referred to herein as a "blood prime" stage and shown in FIG. 4, selected components of the fluid flow circuit 12 are primed using blood from a blood source. This is in contrast to typical apheresis devices, which employ a separately provided fluid (e.g., anticoagulant or saline) to prime a fluid flow circuit, though it is also within the scope of the present disclosure for the fluid flow circuit 12 to be primed using a more conventional priming fluid. The blood source is shown in FIG. 4 as the whole blood container 44, but may alternatively be a living donor. Thus, it should be understood that the term "whole blood" may refer to blood that either includes or omits an anticoagulant fluid.

During the blood prime stage, whole blood is drawn into the fluid flow circuit 12 from the blood source (the whole blood container 44 in the embodiment of FIG. 4) via line L1 by operation of the first pump 16 (which may be referred to as the "whole blood pump"). Valve 38*c* is closed, which directs the blood through pressure sensor 40*c* and into line L2. The blood passes through air trap 60, pressure sensor 40*a* (which measures the pressure of the processing chamber 52), and optical sensor 34 before flowing into the processing chamber 52, which is positioned within the centrifuge 22 of the processing device 10.

The centrifuge 22 may be stationary during the blood prime stage or may instead be controlled by the controller of the processing device 10 to spin at a low rotation rate (e.g., on the order of approximately 1,000-2,000 rpm). It may be advantageous for the centrifuge 22 to rotate during the blood prime stage in order to create enough g-force to ensure that the air in the processing chamber 52 (which includes air already present in the processing chamber 52, along with air moved into the processing chamber 52 from lines L1 and/or L2 by the flow of blood) is forced towards the low-g (radially inner) wall of the processing chamber 52. Higher centrifuge rotation rates, such as 4,500 rpm (which is required for steady state separation, as will be described) may be undesirable as air blocks (in which air gets stuck and cannot be forced out of the processing chamber 52, causing pressure to rise) are more likely at higher g-forces.

The blood entering the processing chamber 52 will move towards the high-g (radially outer) wall of the processing chamber 52, displacing air towards the low-g wall. A plasma outlet port of the processing chamber 52 is associated with the low-g wall of the processing chamber 52, such that most of the air will exit the processing chamber 52 via the plasma outlet port and associated line L3, although some air may also exit the processing chamber 52 via a red blood cell outlet port associated with the high-g wall of the processing chamber 52.

Valves 38*b* and 38*d* are closed, while the second pump 18 (which may be referred to as the "plasma pump") is active and the third pump 20 (which may be referred to as the "additive pump") is inactive. This directs the air exiting the processing chamber 52 via the red blood cell outlet port through associated line L4 and pressure sensor 40*b*, into line L5 and then into line L14. Valve 38*a* is open, while clamp 24*b* is closed, such that the air flowing through line L14 will flow and then meet up with the air flowing through line L3 (i.e., the air that exits the processing chamber 52 via the plasma outlet port). The combined air will flow through line L7 and open clamp 24*c*, into the plasma collection container 48.

It should be understood that, in FIGS. 4-17, arrows on the containers represent the direction of fluid flow between the container and the conduit connected to the container. For example, line L7 is shown as being connected to the top of the plasma collection container 48, such that a downward arrow (as in FIG. 4) represents downward fluid flow into the plasma collection container 48. In contrast, line L1 is shown as being connected to the bottom of the whole blood container 44, such that a downward arrow (as in FIG. 4) represents downward fluid flow out of the whole blood container 44.

The flow of air out of the processing chamber 52 via either outlet port is monitored by the optical sensor 34, which is capable of determining the optical density of the fluid flowing through the monitored lines and discerning between air and a non-air fluid in lines L3 and L4. When a non-air fluid is detected in both lines L3 and L4, the controller of the processing device 10 will end the blood prime stage and move on to the next stage of the procedure. The amount of blood drawn into the fluid flow circuit 12 from the blood source during the blood prime stage will vary depending on a number of factors (e.g., the amount of air in the fluid flow circuit 12), but may be on the order of approximately 50 to 100 mL. The blood prime stage may take on the order of one to two minutes.

The next stage (shown in FIG. 5) is referred to herein as the "establish separation" stage. Once non-air fluid has been detected in lines L3 and L4, the rotational speed of the centrifuge 22 will be increased to a rate that is sufficient to separate blood into packed red blood cells and platelet-poor plasma (which may be in the range of approximately 4,500 to 5,500 rpm, for example). To produce a plasma product that is low in platelets, it may be advantageous for the processing chamber 52 to be configured with a plasma outlet port that is spaced from and positioned downstream of the blood inlet port, rather than being positioned adjacent to the blood inlet port. Such a configuration allows the platelets to settle down into a distinct layer between the plasma and the red blood cells (commonly referred to as a "buffy coat") before the plasma is removed from the processing chamber 52, thus allowing the separated plasma to be platelet-depleted. As for the whole blood pump 16, it continues to operate, but no additional blood is drawn into the fluid flow circuit 12 from the blood source during the establish separation stage (as will be described).

In embodiments in which the blood source includes (in the case of a whole blood container) or provides (in the case of a living donor) only a single unit of whole blood (approximately 500 mL), the system must work with a finite fluid volume. To avoid product loss or quality issues, the plasma and red blood cells initially separated from the blood in the processing chamber 52 and removed from the processing chamber 52 are not directed to their respective collection containers, but are instead mixed together to form recombined whole blood and recirculated back into the processing chamber 52.

More particularly, during the establish separation stage, separated plasma will exit the processing chamber 52 via the plasma outlet port and associated line L3. Clamps 24*b* and 24*c* are closed during this stage, while valve 38*a* remains open, which directs the plasma from line L3 into line L14. Separated red blood cells exit the processing chamber 52 via the red blood cell outlet port and associated line L4, while the buffy coat remains in the processing chamber 52. In the illustrated embodiment, there is no pump associated with line L4, such that the red blood cells exit the processing chamber 52 at a rate that is equal to the difference between the rate of the whole blood pump 16 and the rate of the plasma pump 18. In alternative embodiments, there may be a pump associated with the red blood cell outlet line instead of the plasma outlet line or a first pump associated with the plasma outlet line and a second pump associated with the red blood cell outlet line.

The additive pump 20 is inactive during this stage, thereby directing the red blood cells from line L4 into line L5. The plasma flowing through line L14 is mixed with the red blood cells flowing through line L5 at a junction of the two lines L5 and L14 to form recombined whole blood. Valve 38*d* is closed, which directs the recombined whole blood into line L8. Valve 38*b* is also closed, which directs the recombined whole blood from line L8 into line L9 and through open valve 38*c*. The whole blood pump 16 draws the recombined whole blood into line L2 from line L9 (rather than drawing additional blood into the fluid flow circuit 12 from the blood source), with the recombined blood passing through air trap 60, pressure sensor 40*a*, and optical sensor 34 before flowing back into the processing chamber 52, where it is again separated into plasma, buffy coat, and red blood cells.

The establish separation stage continues until steady state separation has been achieved, which may take on the order of approximately one to two minutes. As used herein, the phrase "steady state separation" refers to a state in which blood is separated into its constituents in the processing chamber 52, with the radial position of the interface between separated components within the processing chamber 52 being at least substantially maintained (rather than moving radially inwardly or outwardly). The position of the interface may be determined and controlled according to any suitable approach, including using an interface detector of the type described in U.S. Patent Application Publication No. 2019/0201916.

Preferably, steady state separation is achieved with the interface between separated components within the processing chamber 52 at a target location. The target location may correspond to the location of the interface at which separation efficiency is optimized, with the precise location varying depending on a number of factors (e.g., the hematocrit of the whole blood). However, in an exemplary embodiment, the target location of the interface may be the position of the interface when approximately 52% of the thickness or width (in a radial direction) of the channel defined by the processing chamber 52 is occupied by red blood cells. In the illustrated embodiment, the position of the interface within the processing chamber 52 may be adjusted by changing the flow rate of the plasma pump 18, with the flow rate being increased to draw more separated plasma out of the processing chamber 52 (which decreases the thickness of the plasma layer within the processing chamber 52) and move the interface toward the low-g wall or decreased to draw less plasma out of the processing chamber 52 (which increases the thickness of the plasma layer within the processing chamber 52) and move the interface toward the high-g wall.

In an exemplary procedure, the controller of the processing device 10 will control the whole blood pump 16 to operate at a constant rate, with the plasma pump 18 initially operating at the same rate, which will quickly increase the thickness of the red blood cell layer within the processing chamber 52 and move the interface toward the low-g wall. The rate of the plasma pump 18 is gradually decreased as the thickness of the red blood cell layer increases and the location of the interface approaches the target location. As described above, the target location of the interface may depend upon the hematocrit of the whole blood, meaning that the rate of the plasma pump 18 (which controls the position of the interface) may also depend on the hematocrit of the whole blood. In one embodiment, this relationship may be expressed as follows:

$$\text{Theoretical plasma pump rate} = \text{whole blood pump rate} - ((\text{whole blood hematocrit} * \text{whole blood pump rate}) / \text{hematocrit of separated red blood cells}) \quad \text{[Equation 1]}$$

The hematocrit of the whole blood may be measured before the procedure begins or by the optical sensor 34 during the procedure, while the hematocrit of the separated red blood cells may be determined during the procedure by the optical sensor 34 monitoring line L4. In practice, the plasma pump rate will typically not remain at the theoretical rate once steady state separation has been achieved, with the interface at the target location, but rather the plasma pump rate will instead tend to "flutter" around the theoretical rate.

Figure 6:
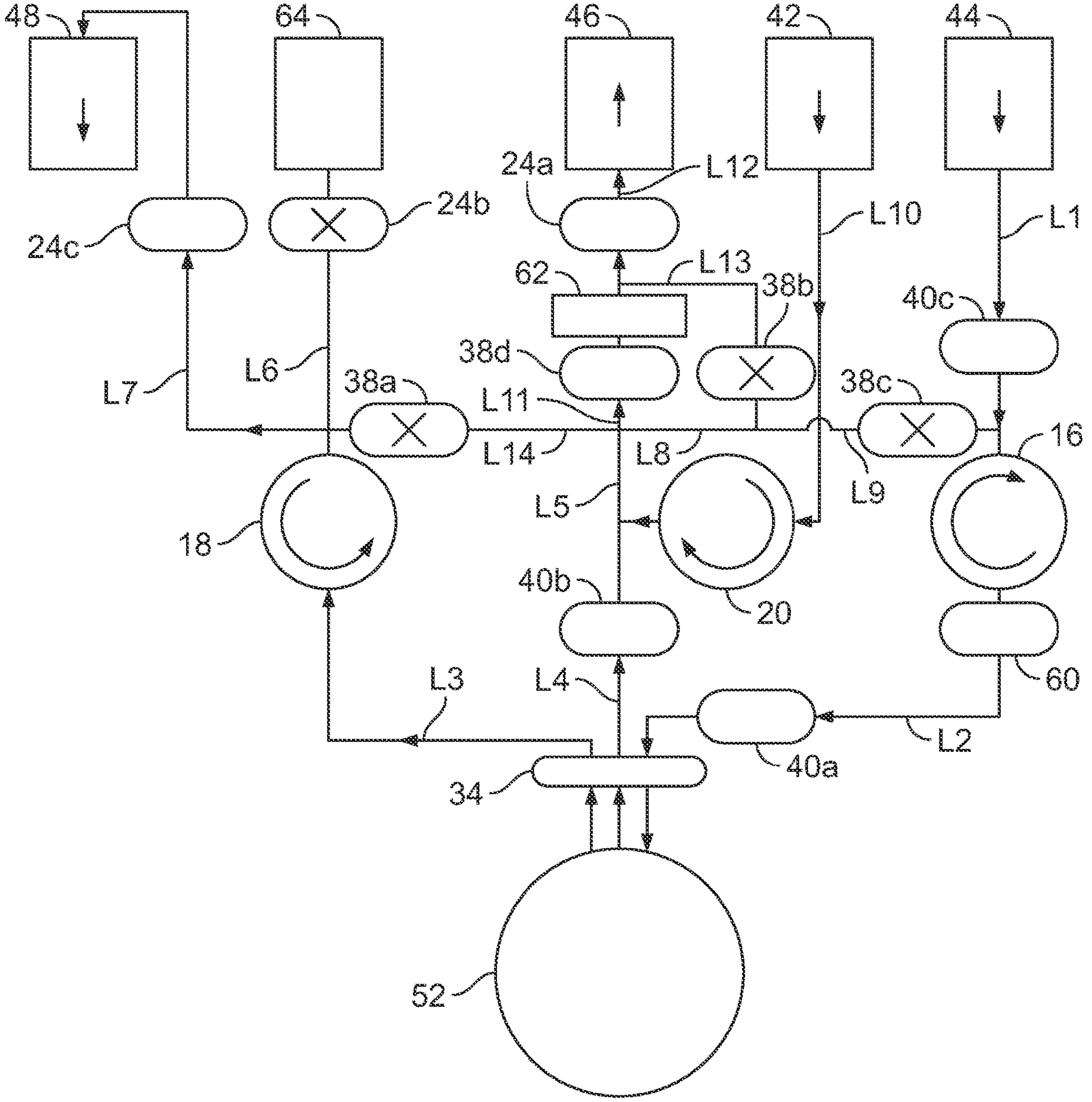
FIG. 6 is a schematic view of the blood processing system of FIG. 3 executing a “collection” stage of an exemplary blood processing procedure, with separated red blood cells being leukoreduced before collection.

Regardless of the particular manner in which the controller of the processing device 10 executes the establish separation stage and arrives at steady state separation, once steady state separation has been established, the controller ends the establish separation stage and advances the procedure to a "collection" stage, which is illustrated in FIG. 6. At the beginning of the collection stage, the centrifuge 22, the whole blood pump 16, and the plasma pump 18 all continue operating at the same rates at which they were operating at the end of the establish separation stage. The valve system of the processing device 10, however, is adjusted to direct the separated plasma and red blood cells to their respective collection containers (rather than recombining them and recirculating them through the centrifuge 22), while causing additional blood to be drawn into the fluid flow circuit 12 from the blood source until a total of one unit or some other target amount of whole blood has been drawn into the fluid flow circuit 12.

More particularly, during the collection stage, valve 38*c* is closed, which causes the whole blood pump 16 to draw additional blood into line L1 from the blood source (which is the whole blood container 44 in the illustrated embodiment, but may be a living donor). The whole blood pump 16 draws the blood from the blood source into line L2 from line L1, with the blood passing through air trap 60, pressure sensor 40*a*, and optical sensor 34 before flowing into the processing chamber 52, where it is separated into plasma, red blood cells, and buffy coat. Most of the platelets of the whole blood will remain in the processing chamber 52 as part of the buffy coat, along with some white blood cell populations (much as mononuclear cells), while larger white blood cells, such as granulocytes, may exit with the packed red blood cells. In addition to the buffy coat, the fluid remaining in the processing chamber 52 may also include a portion of the plasma and a portion of red blood cells.

At least a portion of the separated plasma exits the processing chamber 52 via the plasma outlet port and associated line L3. Valve 38*a* is closed, which directs the plasma from line L3 into line L7, through open clamp 24*c*, and into the plasma collection container 48.

Figure 7:
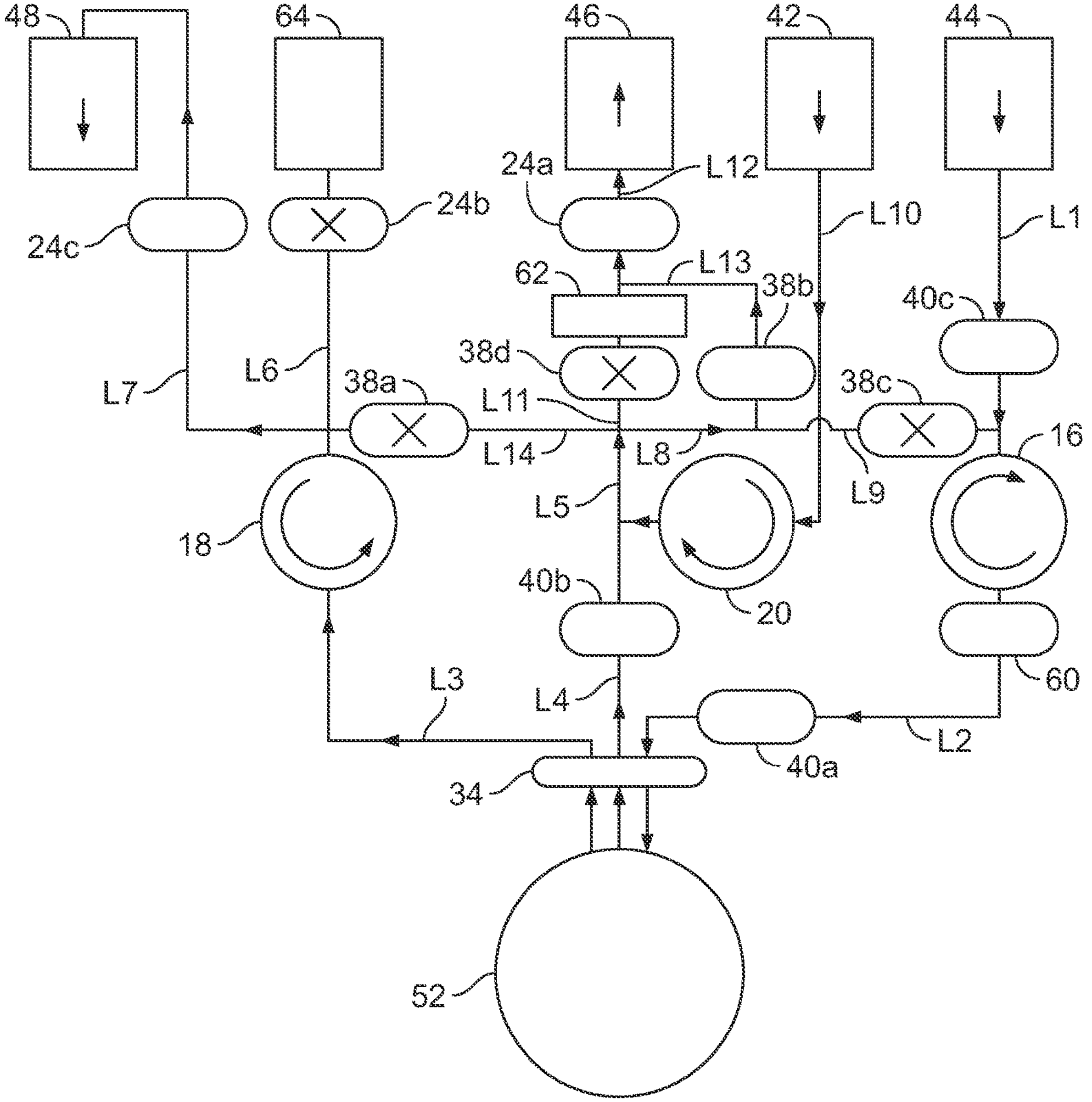
FIG. 7 is a schematic view of a variation of the “collection” stage of FIG. 6 in which the separated red blood cells are not leukoreduced before collection.

As for the separated red blood cells, at least a portion of them exits the processing chamber 52 via the red blood cell outlet port and associated line L4. The additive pump 20 is operated by the controller to draw an additive solution (which is ADSOL® in one exemplary embodiment, but may be some other red blood cell additive) from the additive solution container 42 via line L10. The red blood cells flowing through line L4 are mixed with the additive solution flowing through line L10 at a junction of the two lines L4 and L10 to form a mixture that continues flowing into and through line L5. The mixture is ultimately directed into the red blood cell collection container 46, but may first be conveyed through a leukoreduction filter 62 (if provided), as shown in FIG. 6. Even if a leukoreduction filter 62 is provided, the valve system may be controlled to cause the mixture to bypass the leukoreduction filter 62 and enter the red blood cell collection container 46 without being leukoreduced, as shown in FIG. 7. It is also within the scope of the present disclosure for the mixture to be routed through the leukoreduction filter 62 at the beginning of the collection stage, with the valve system being reconfigured during the collection stage to cause the mixture to bypass the leukoreduction filter 62, such that only a portion of the collected red blood cells are leukoreduced.

In the configuration of FIG. 6 (in which the mixture is leukoreduced), valves 38*a*, 38*b*, and 38*c* are closed, while valve 38*d* is open, which directs the mixture from line L5 into line L11. The mixture flows through open valve 38*d* and the leukoreduction filter 62 and into line L12. The leukoreduced mixture then flows through open clamp 24*a* and into the red blood cell collection container 46.

In the configuration of FIG. 7 (in which the mixture is not leukoreduced), valves 38*a*, 38*c*, and 38*d* are closed, while valve 38*b* is open, which directs the mixture from line L5 into line L8 and then into line L13. The mixture flows through open valve 38*b* and into line L12, bypassing the leukoreduction filter 62. The non-leukoreduced mixture then flows through open clamp 24*a* and into the red blood cell collection container 46.

As described above, the mixture may be routed through the leukoreduction filter 62 at the beginning of the collection stage (as in FIG. 6), with the valve system being reconfigured during the collection stage to cause the mixture to bypass the leukoreduction filter 62 (as in FIG. 7), such that only a portion of the collected red blood cells are leukoreduced. In one embodiment, pressure sensor 40*b* monitors the pressure of the leukoreduction filter 62. If the pressure sensor 40*b* detects that the pressure of the leukoreduction filter 62 has risen above a predetermined pressure threshold (which may be indicative of filter blockage), the controller may reconfigure the valve system (from the configuration of FIG. 6 to the configuration of FIG. 7) to cause the mixture to bypass the leukoreduction filter 62. The system may then alert the operator that the red blood cell product was not leukoreduced.

Regardless of whether the collected red blood cells have been leukoreduced (or only partially leukoreduced), the collection stage continues until a target amount of whole blood (which may be one unit of whole blood or any other amount) has been drawn into the fluid flow circuit 12 from the blood source. In the case of a whole blood container 44 being used as a blood source (as in the illustrated embodiment) the collection stage will end when the whole blood container 44 (which is initially provided with one unit of whole blood) is empty, with different approaches possibly being employed to determine when the whole blood container 44 is empty. For example, in one embodiment, pressure sensor 40*c* monitors the hydrostatic pressure of the whole blood container 44. An empty whole blood container 44 may be detected when the hydrostatic pressure measured by pressure sensor 40*c* is at or below a threshold value. Alternatively (or additionally), the weight of the whole blood container 44 may be monitored by a weight scale, with an empty whole blood container 44 being detected when the weight is at or below a threshold value. In the case of a living donor (or in the event that the whole blood container 44 is provided with more than one unit of blood), the volumetric flow rate of the whole blood pump 16 may be used to determine when one unit of whole blood has been drawn into the fluid flow circuit 12.

At the end of the collection stage, the buffy coat has been sequestered within the processing chamber 52 and may simply be harvested. The buffy coat could then be pooled with 3-4 additional buffy coats (4-5 total) and further separated to produce a clean platelet product. However, it may be advantageous to instead harvest platelets (platelet concentrate) from the processing chamber 52 in a manner that does not require further (secondary) processing to produce a platelet product. By harvesting platelet concentrate instead of the buffy coat, there is no additional platelet loss during the secondary procedure that is required following pooling of multiple buffy coats. Due to there being less platelet loss, it may be possible for fewer units of blood to be processed to produce a platelet product, which may include a platelet product being formed by combining platelet concentrate from 3-4 units of blood, rather than the 4-5 units of blood required to produce a comparable platelet product using pooled buffy coats.

In order to collect platelet concentrate, the controller ends the collection stage and moves to a "platelet resuspension" stage. In one exemplary embodiment, there are two separate phases in the platelet resuspension stage, with the fluid in the processing chamber 52 (which includes the buffy coat) being mixed to form a homogenous fluid during the first phase, followed by separation of the fluid into platelet concentrate and red blood cells during the second phase. While a two-phase platelet resuspension stage will be described in greater detail, it should be understood that it is merely exemplary and that it is within the scope of the present disclosure for the platelet resuspension stage to have different phases or a different number of phases.

Figure 5:
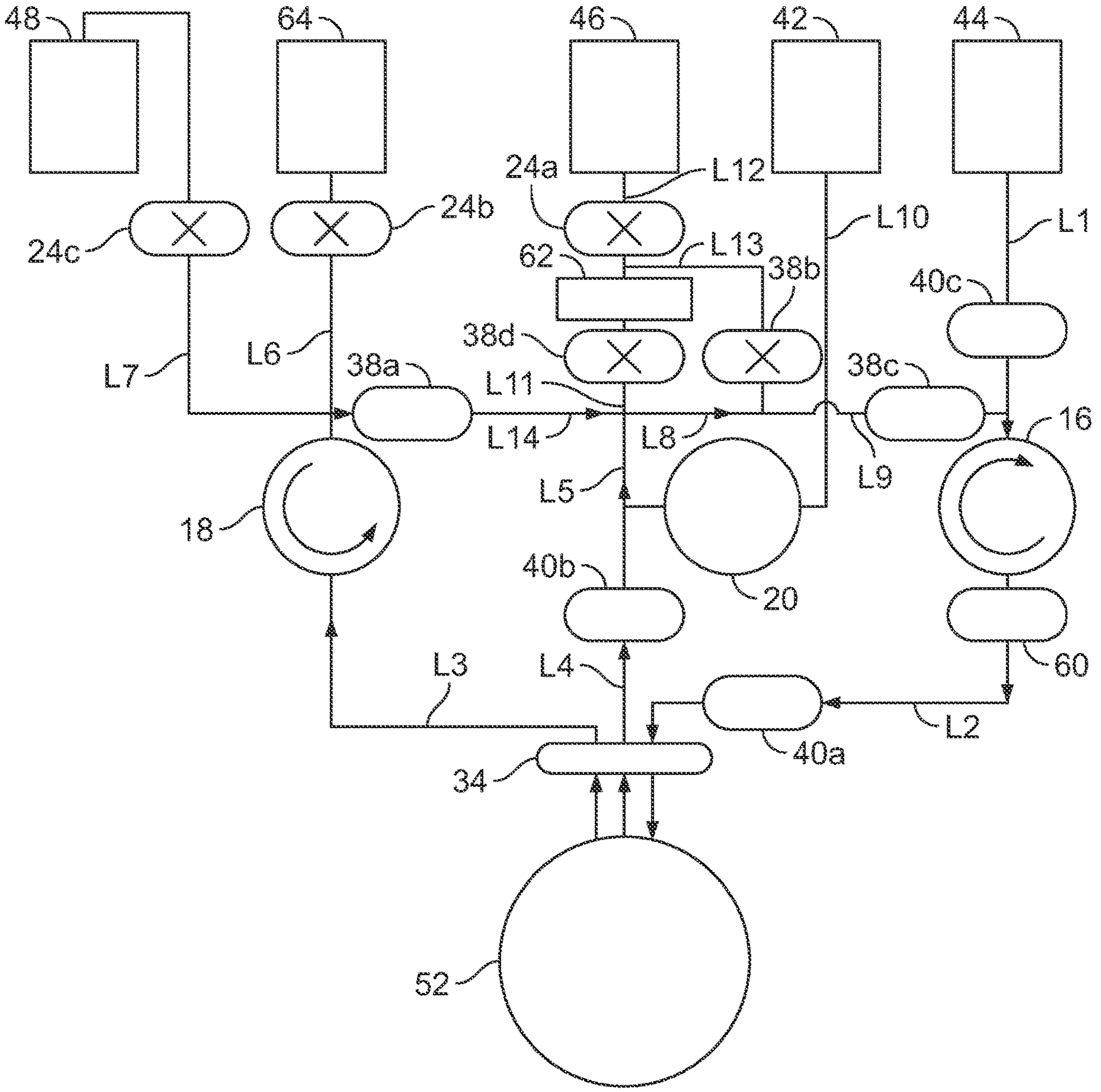
FIG. 5 is a schematic view of the blood processing system of FIG. 3 executing “establish separation” and “platelet resuspension” stages of an exemplary blood processing procedure.

In the first phase of the exemplary two-phase platelet resuspension stage, the pump system and the valve system return to the states they were in during the establish separation stage, as illustrated in FIG. 5. Although fluid flow is directed along the same path through the fluid flow circuit 12 during the establish separation stage and the first phase of the platelet resuspension stage, it will be understood that the composition of the fluid moving through the fluid flow circuit 12 is not the same. Additionally, the centrifuge 22 is rotated at different rates during the establish separation stage and the first phase of the platelet resuspension stage (as will be described), with the fluid being separated during the establish separation stage, but mixed during the first phase of the platelet resuspension stage.

More particularly, in order to move from the collection stage to the first phase of the platelet resuspension stage, clamps **24*a* and 24*c* are closed (along with valves 38*b* and 38*d*), preventing further collection of separated plasma and separated red blood cells. The whole blood pump 16 and plasma pump 20 remain active, while the additive pump 20 is deactivated and valves 38*a* and 38*c* are opened, which causes fluid to circulate through the processing chamber 52, as described above with regard to the establish separation stage. During this first phase of the platelet resuspension stage, the whole blood pump 16 may rotate faster (at 100 ml/min in one example) than the plasma pump 18 (which may operate at 80 ml/min in the same example), with the difference of the operational rates of the two pumps 16 and 18 being the rate at which fluid exits the processing chamber 52 via line L4** (i.e., at 20 ml/min in the example).

While the centrifuge 22 is active during the establish separation stage (and the subsequent collection stage), it is inactive during the first phase of the platelet resuspension stage and does not rotate the processing chamber 52. This causes the fluid in the processing chamber 52 (which includes the buffy coat) to become mixed as it circulates, eventually forming a homogeneous mixture. The homogeneous mixture may have a hematocrit in the range of approximately 40-60% and a platelet concentration of approximately 2000e3/uL, with the exact composition of the mixture depending in part on the composition of the whole blood being processed.

The first phase of the resuspension stage may continue for a predetermined amount of time known to effectively mix the fluid. Alternatively, the first phase may continue until the optical sensor 34 detects a homogenous mixture in lines L2, L3 and L4, determining that the resuspension was effective. In either case, after determining that a suitable homogenous mixture has been formed, the controller will move into the second phase of the resuspension stage.

During the second phase of the platelet resuspension stage (in which the pump and valve systems may be configured as during the first phase, and as shown in FIG. 5), the centrifuge 22 begins to rotate to promote separation of the homogenous fluid. While the centrifuge 22 is rotated at a "hard spin" during the establish separation and collection stages (which is on the order of 4,500 to 5,500 rpm), it rotates more slowly during the second phase of the platelet resuspension stage (such as in the range of 2,000 to 3,000 rpm, which may be considered a "soft spin"). The slower rotation rate enables separation of the homogenous fluid into plasma and red blood cell fractions, but does not provide enough g's to cause sedimentation of the platelets, thus allowing them to remain in the plasma fraction to form a platelet concentrate. The flow rates of the separated fluid fractions out of the processing chamber 52 via lines L3 and L4 may remain the same as during the first phase of the platelet resuspension stage or be set at different levels, either of which may include one or both of the flow rates being incrementally adjusted (as necessary) until the fluid exiting the processing chamber 52 via line L3 is free of red blood cells.

Throughout the second phase of the platelet resuspension stage, the platelet concentrate exiting the processing chamber 52 via line L3 and the red blood cells exiting via line L4 are recombined in line L8 and recirculated through the processing chamber 52 by the whole blood pump 16. The second resuspension phase may continue for a predetermined amount of time known to allow for full resuspension of platelets into platelet concentrate or until the optical sensor 34 detects the platelet content of the fluid flowing through line L3 to be acceptable to transition to the next stage.

The next stage of the procedure is a "platelet harvest" stage during which the platelet concentrate (containing the resuspended platelets) is pushed or conveyed out of the processing chamber 52 for collection in the platelet concentrate collection container 64. This may be accomplished in any of a number of ways, including using either whole blood from the whole blood source 44 (with two variations of such an approach being shown in FIGS. 8 and 9) or separated red blood cells from the red blood cell collection container 46 (with two variations of such an approach being shown in FIGS. 10 and 11).

When whole blood is used to harvest the platelet concentrate, clamps **24*a* and 24*b* are opened, while valves 38*a* and 38*c* are closed. Red blood cells are collected when whole blood is used to harvest the platelet concentrate, meaning that one of valves 38*b* and 38*d* will be opened, depending on whether the red blood cells are to be leukoreduced (FIG. 8) or not (FIG. 9) before reaching the red blood cell collection container 46. In either case, whole blood from the blood source 44 is pumped into the processing chamber 52 by the whole blood pump 16 via lines L1 and L2. The whole blood pump 16 and the plasma pump 18 (which is also active during the platelet harvest stage) may be set to predetermined constant rates or the whole blood pump 16 may operate at a constant rate while the operational rate of the plasma pump 18 is varied by the controller based on input from the interface detector. The centrifuge 22 may continue to rotate the processing chamber 52** at the same rate as during the second phase of the platelet resuspension stage to enable sedimentation of red blood cells and white blood cells, but not platelets, from the plasma fraction to produce the platelet concentrate.

As the newly introduced whole blood separates into red blood cells and plasma (platelet concentrate) in the processing chamber 52, the new plasma from the whole blood will act to force the platelet concentrate or upstream plasma fraction (containing the resuspended platelets) out of the chamber 52 via line L3 and through line L6 and open clamp 24*b*, into the platelet concentrate collection container 64. Throughout the platelet harvest stage, the interface position (red blood cell bed thickness) may also be increased by the controller to further promote removal of the platelet concentrate from the processing chamber 52.

Figure 8:
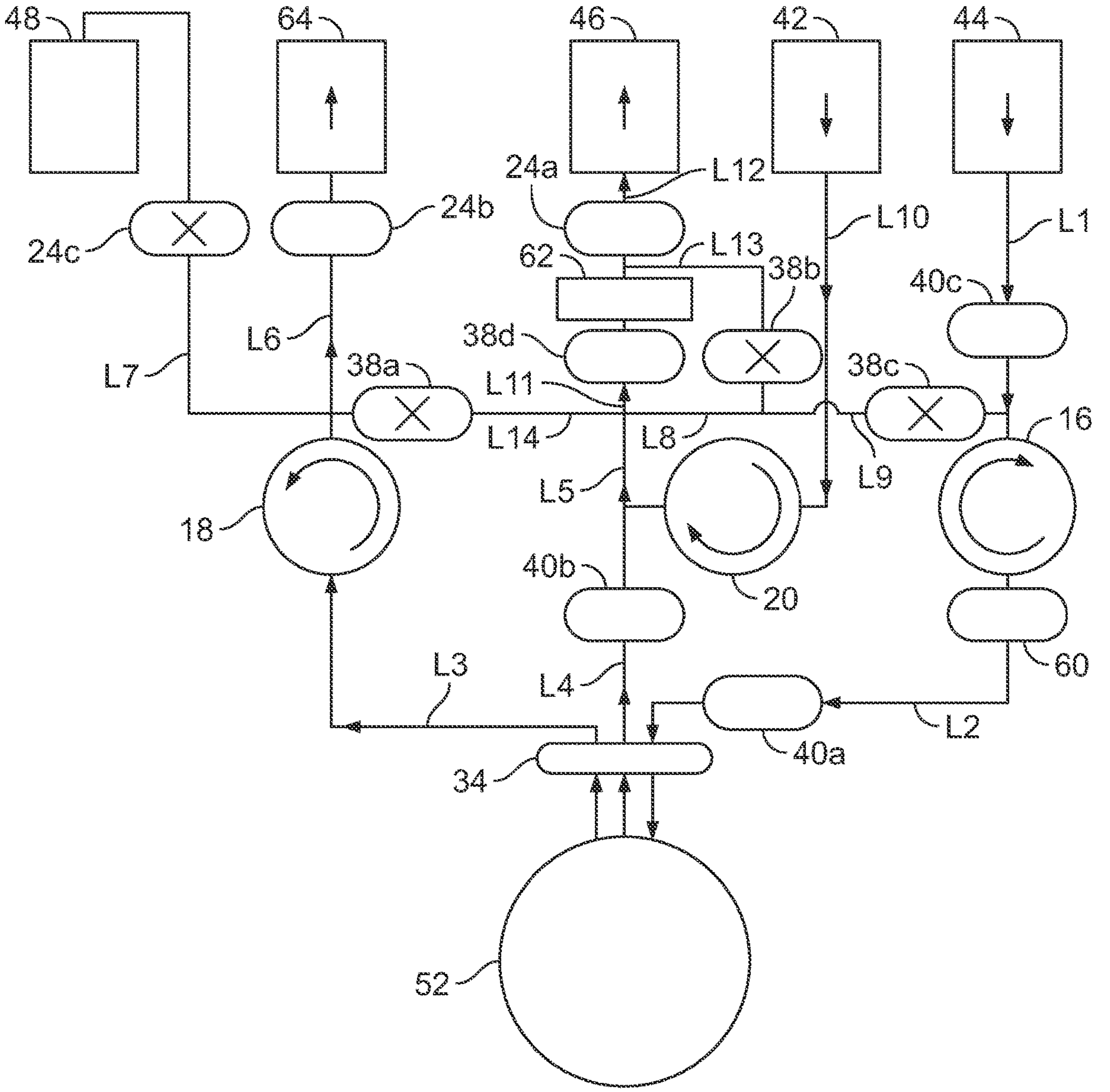
FIG. 8 is a schematic view of the blood processing system of FIG. 3 executing a “platelet harvest” stage of an exemplary blood processing procedure, with platelets harvested using whole blood and with separated red blood cells being leukoreduced before collection.
Figure 9:
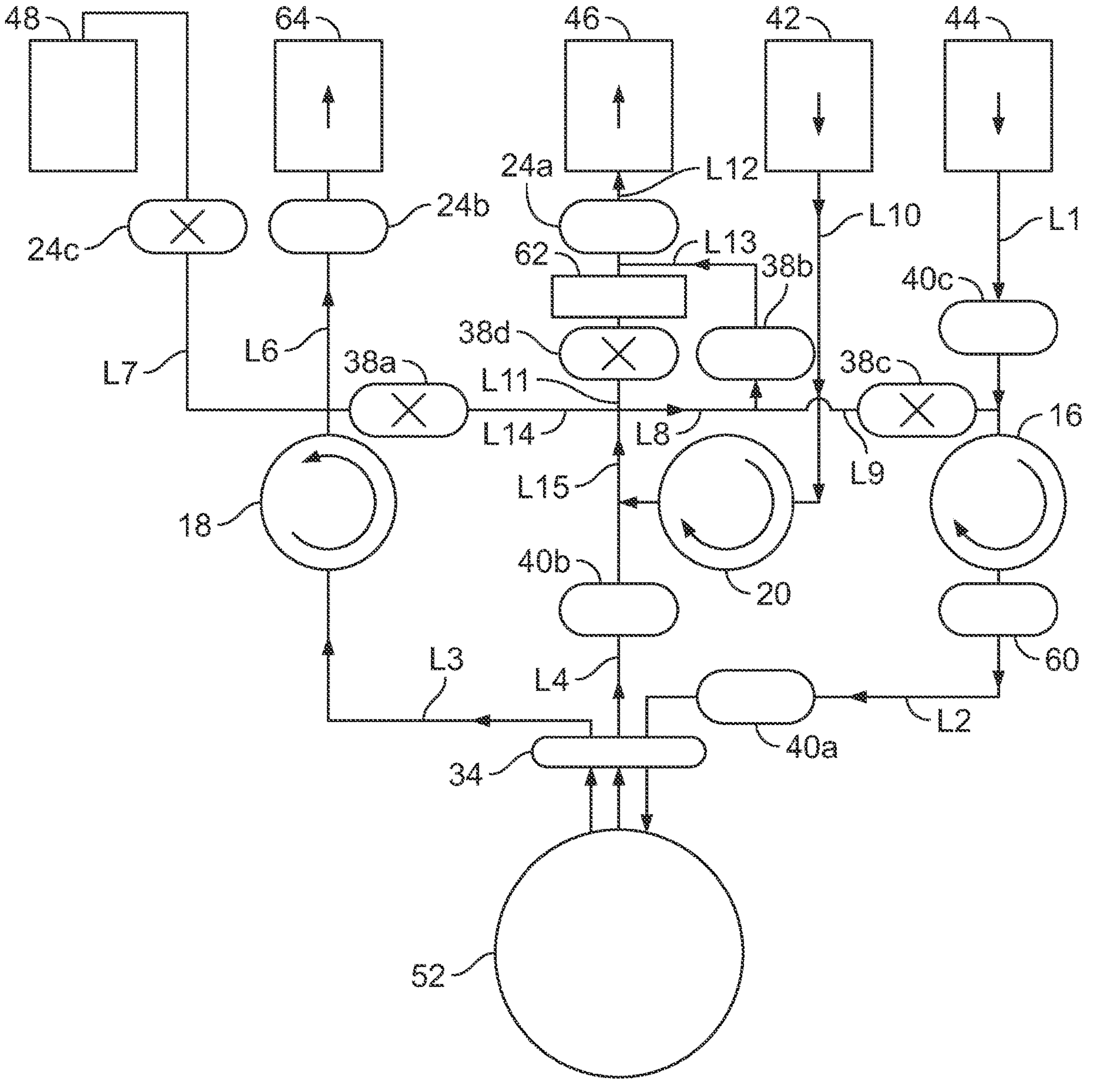
FIG. 9 is a schematic view of a variation of the “platelet harvest” stage of FIG. 8 in which the separated red blood cells are not leukoreduced before collection.

As for the separated red blood cells, at least a portion of them exit the processing chamber 52 via the red blood cell outlet port and associated line L4. The additive pump 20 is operated by the controller to draw additive solution from the additive solution container 42 via line L10, with the red blood cells flowing through line L4 being mixed with the additive solution at a junction of lines L4 and L10 to form a mixture that continues flowing into and through line L5. The mixture is ultimately directed into the red blood cell collection container 46, optionally flowing through a leukoreduction filter 62 (if provided), as shown in FIG. 8. As described above with regard to the collection stage, even if a leukoreduction filter 62 is provided, the valve system may be controlled to cause the mixture to bypass the leukoreduction filter 62 and enter the red blood cell collection container 46 without being leukoreduced, as shown in FIG. 9. This may also include the mixture being routed through the leukoreduction filter 62 at the beginning of the platelet harvest stage, with the valve system being reconfigured during the platelet harvest stage to cause the mixture to bypass the leukoreduction filter 62, such that only a portion of the collected red blood cells are leukoreduced.

Regardless of whether the red blood cells are leukoreduced, the platelet harvest stage may continue until an action or status triggers the end. For instance, the controller may be configured to end the platelet harvest stage when the whole blood container 44 is empty, when the optical sensor 34 determines that the platelet content of the plasma fraction flowing through line L3 is below a predetermined threshold (indicating that the plasma fraction has transitioned from the platelet concentrate to the plasma separated from the newly introduced whole blood), when the interface detector detects the interface at a target location, when the optical sensor 34 detects the presence of red blood cells in line L3 (indicating that the entire plasma fraction has been evacuated), or any combination of these events.

Figure 10:
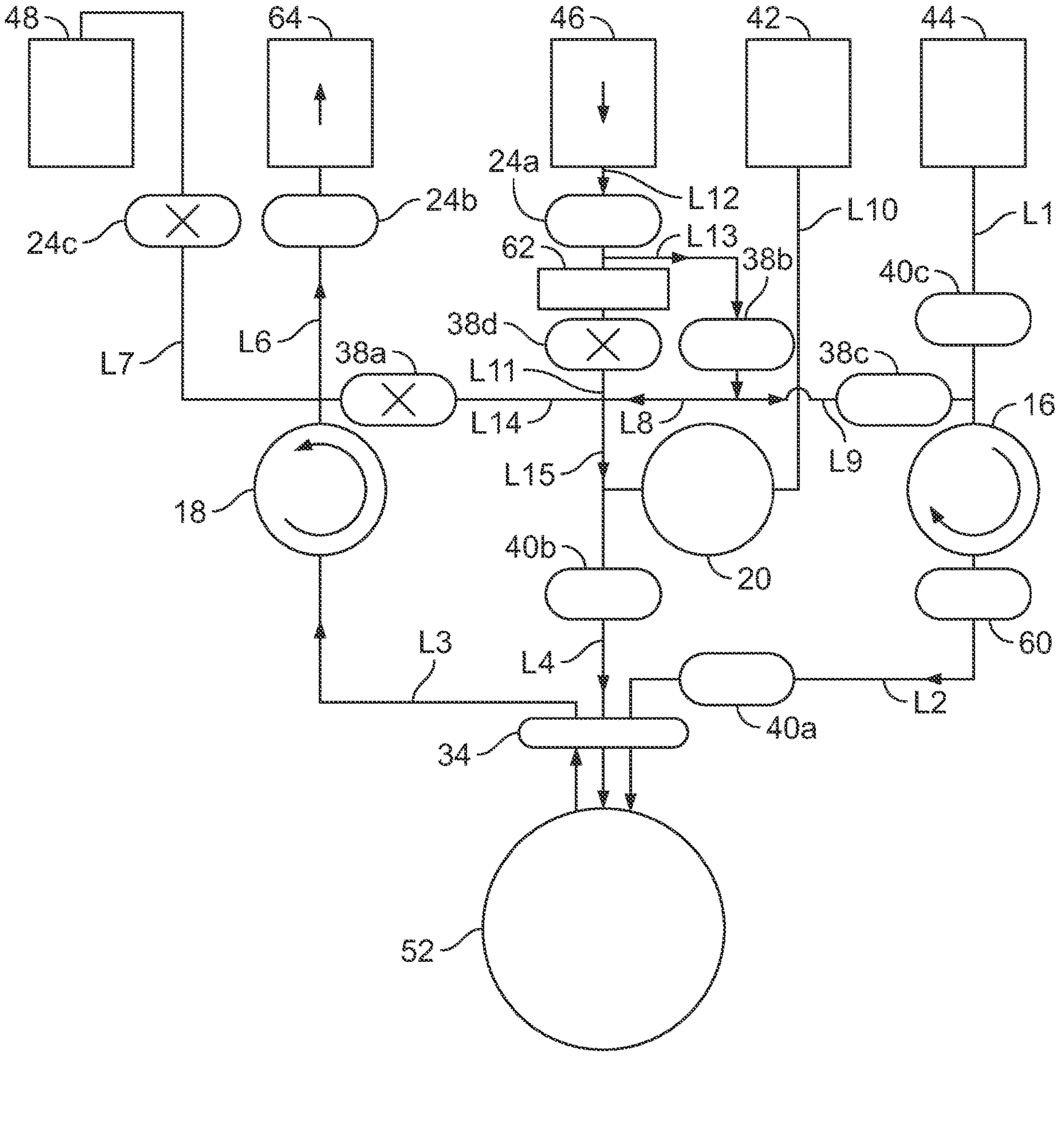
FIG. 10 is a schematic view of a variation of the “platelet harvest” stage of FIG. 8, with platelets harvested using collected red blood cells and a whole blood pump.
Figure 11:
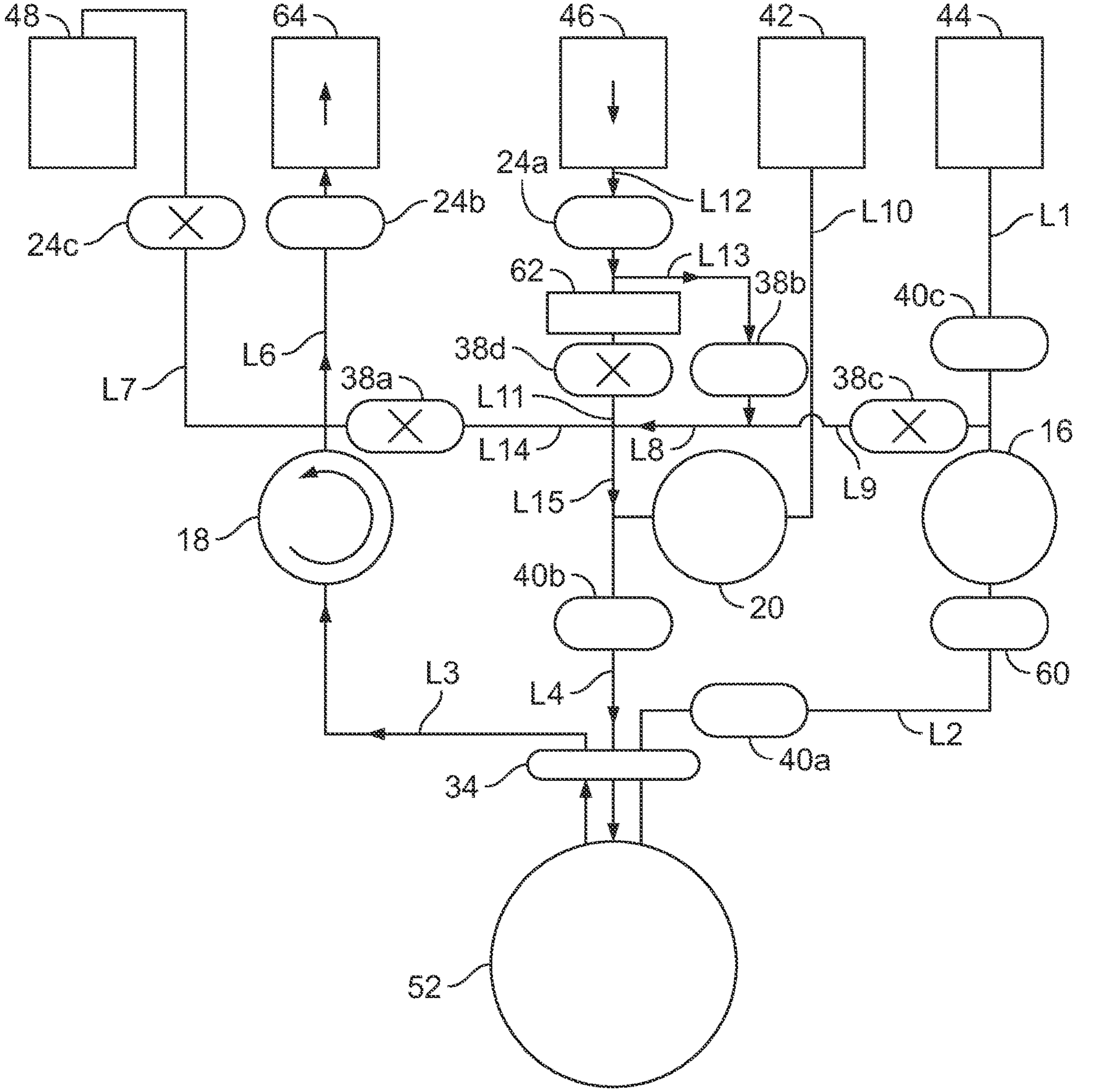
FIG. 11 is a variation of the “platelet harvest” stage of FIG. 10, with the whole blood pump being inactive.

Alternatively, as noted above, the platelet concentrate may be harvested using collected red blood cells instead of whole blood (e.g., if all of the available blood from the blood source has been processed), with FIGS. 10 and 11 showing two variations of such an approach. In the variation of FIG. 10, the whole blood pump 16 is used to harvest the platelet concentrate, whereas it is inactive in the variation of FIG. 11. In both variations, to transition from the platelet resuspension stage to the platelet harvest stage, clamps 24*a* and 24*b* and valve 38*b* are opened, while valve 38*a* is closed. Clamp 38*c* remains open when the whole blood pump 16 is operative (in the variation of FIG. 10), whereas it is closed when the whole blood pump 16 is inactive (in the variation of FIG. 11).

In the variation of FIG. 10, red blood cells are removed from the red blood cell collection container 46 and travel into the processing chamber 52 via both lines L2 and L4. In the illustrated embodiment, the plasma pump 18 must be set to a rate greater than that of the whole blood pump 16 to enable red blood cells to enter the processing chamber 52 via line L4 (because there is no pump associated with line L4). The whole blood pump 16 and the plasma pump 18 are set to predetermined rates (which may be the same or different from the operational rates at the end of the platelet resuspension stage), while the centrifuge 22 continues to rotate the processing chamber 52 at a rate calculated to enable sedimentation of red blood cells and white blood cells, but not platelets, from the plasma fraction to produce the platelet concentrate.

In the variation of FIG. 11 (in which the whole blood pump 16 is inactive and valve 38*c* is closed), the portion of the red blood cells exiting the red blood cell collection container 46 will enter the processing chamber 52 via only line L4. The plasma pump 18 may be set to any suitable rate, which may be the same or different from its operational rate at the end of the platelet resuspension stage. As in the other variations of the platelet harvest stage, the centrifuge 22 continues to rotate the processing chamber 52 at a rate calculated to produce the platelet concentrate.

In both variations, the red blood cells entering the processing chamber 52 will act to increase the red blood cell bed thickness, thus evacuating the platelet concentrate out of the chamber 52 via line L3 and through line L6 and open clamp 24*b*, into the platelet concentrate collection container 64. If employed, a platelet harvest stage using red blood cells may be ended based on conditions similar to those described above with regard to the variations using whole blood to harvest the platelet concentrate (e.g., when the red blood cell collection container 46 is empty and/or when the optical sensor 34 detects the presence of red blood cells in line L3).

In any of the variations of the platelet harvest stage, the optical sensor 34 may estimate the concentration of platelets in the fluid in the platelet concentrate collection container 64. The platelet concentration may be multiplied by the volume of fluid in the platelet concentrate collection container 64 (which may be determined using a weight scale, for example) to estimate of the quantity of platelets in the platelet concentrate collection container 64. This information may be used to enable efficient pooling of multiple volumes of platelet concentrate. For example, if three platelet concentrate collection containers with estimated platelet counts of 1.1e11, 1.3e11, and 0.9e11 are available, a platelet product may be formed by pooling only those three volumes of platelet concentrate. On the other hand, if three platelet concentrate collection containers with estimated platelet counts of 0.7e11, 0.8e11, and 0.8e11 are available, then it can be determined that an additional volume of platelet concentrate (ideally, one having a relatively low platelet count, such as 0.8e11) will also be required to achieve the 3.0e11 therapeutic dosing threshold. It will thus be seen that the ability to estimate platelet counts for pooling purposes makes significant procedural and monetary benefits possible.

Figure 12:
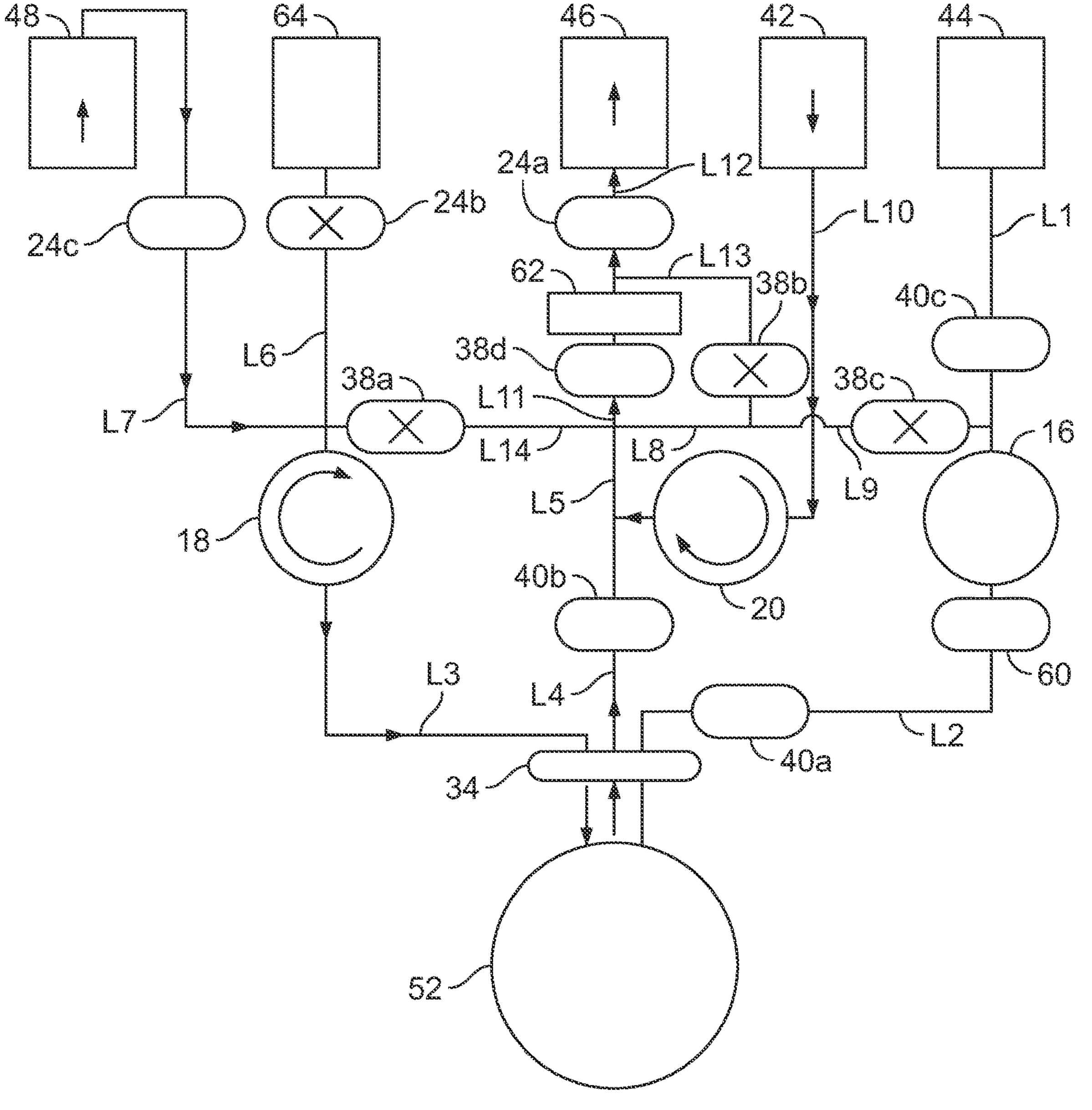
FIG. 12 is a schematic view of the blood processing system of FIG. 3 executing a “red blood cell recovery” stage of an exemplary blood processing procedure, with recovered red blood cells being leukoreduced before collection.
Figure 13:
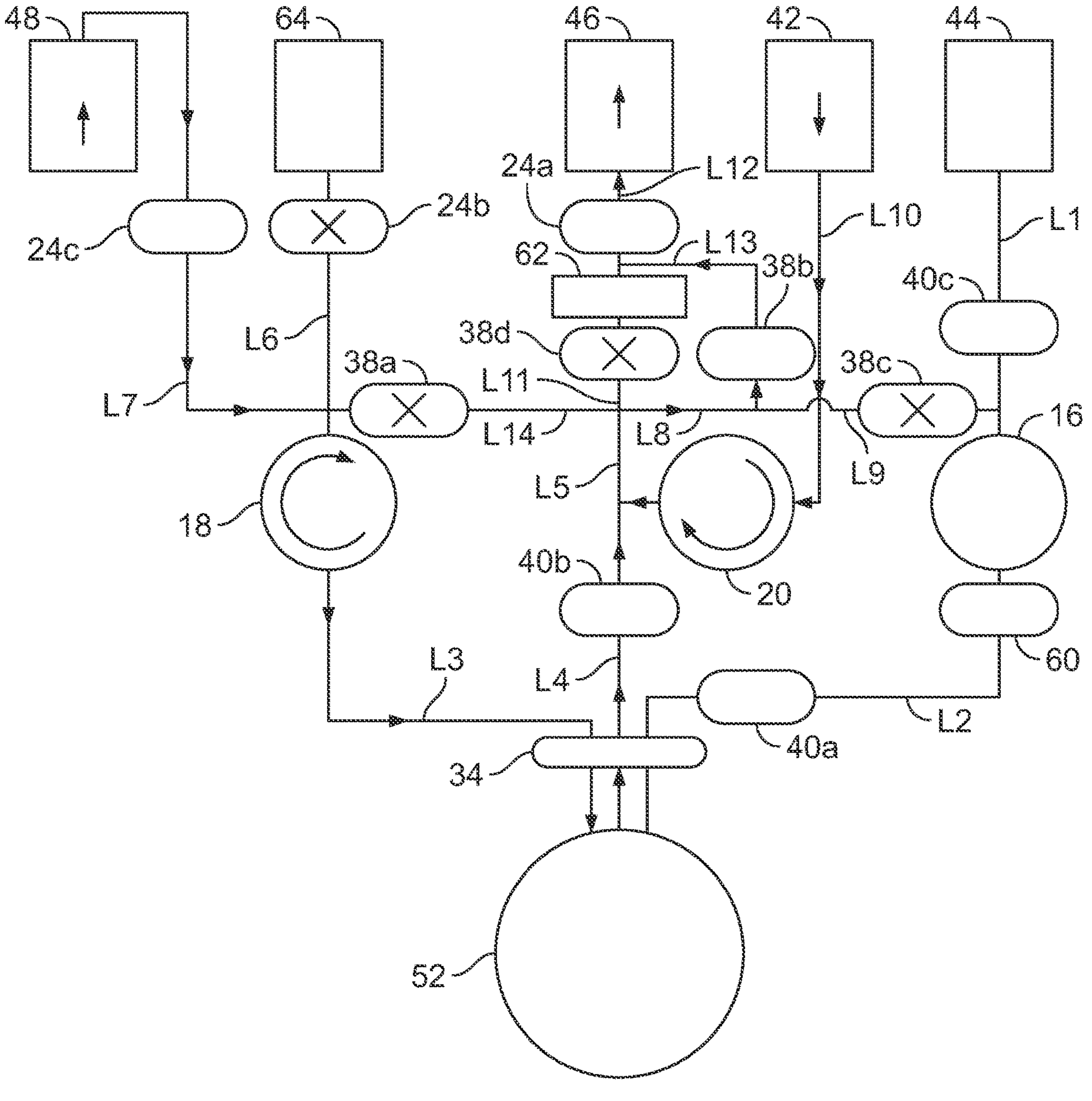
FIG. 13 is a schematic view of a variation of the “red blood cell recovery” stage of FIG. 12 in which the separated red blood cells are not leukoreduced before collection.

After the platelet resuspension and platelet harvest stages, the controller will transition the procedure to a “red blood cell recovery” stage. During the red blood cell recovery stage, air from the plasma collection container 48 (which was conveyed there during the blood prime stage) is used to recover the red blood cells from the processing chamber 52 to reduce product loss. FIG. 12 shows a variation of the red blood cell recovery stage in which the recovered red blood cells are leukoreduced, while FIG. 13 shows a variation in which they are not.

In both illustrated variations, the whole blood pump 16 is deactivated (if not already inactive, which it is in the variation of the platelet harvest stage shown in FIG. 11), while the plasma pump 18 is operated in a reverse direction (with respect to its direction of operation up to this stage of the procedure). This draws the air from the plasma collection container 48 and into line L7. Valve 38*a* is closed, while clamp 24*c* is open, which directs the air through line L7, into and through line L3, and into the processing chamber 52 via the plasma outlet port. On account of the air flowing through the plasma outlet port, it will enter the processing chamber 52 at the low-g side. As additional air is introduced into the processing chamber 52, it will move from the low-g wall towards the high-g wall, thus displacing any liquid content through the red blood cell outlet port at the high-g side and into line L4. During this stage, the centrifuge 22 may be operated at a slower rate (e.g., in the range of approximately 1,000-2,000 rpm) to decrease the risk of an air blockage (as during the blood prime stage).

The additive pump 20 is activated (if not already active, which it is in the variations of the platelet harvest stage shown in FIGS. 8 and 9), drawing additive solution from the additive solution container 42 and through line L10, to be mixed with the contents of the processing chamber 52 flowing through line L4 at the junction of the two lines L4 and L10. The mixture continues flowing into and through line L5. Depending on whether the fluid is to be leukoreduced (FIG. 12) or not (FIG. 13), the valve system is arranged in the appropriate configuration to direct the mixture toward the red blood cell collection container 46. As described above with regard to the collection stage, it is possible for the controller to change the configurations of the valve system from the configuration shown in FIG. 12 to the configuration of FIG. 13 during the red blood cell recovery stage to stop leukoreduction of the mixture (e.g., if the pressure of the leukoreduction filter 62 becomes too great).

Regardless of whether the mixture is filtered, it flows into line L12, through open clamp 24*a*, and into the red blood cell collection container 46. The red blood cell recovery stage continues until the red blood cells have been removed from the processing chamber 52. This may be determined in any of a number of ways without departing from the scope of the present disclosure. In one embodiment, the red blood cell recovery stage continues until a predetermined volume of fluid (corresponding to the volume of red blood cells remaining in the processing chamber 52) has been conveyed out of the processing chamber 52. This volume may be calculated for example, by determining the volume of red blood cells present in the volume of blood that has been processed (which is one unit in one embodiment), which may be determined based on the hematocrit of the blood. The volume of red blood cells that have already been conveyed into the red blood cell collection container 46 (which may be determined based on the weights of the red blood cell collection container 46 and the additive solution container 42 at the end of the platelet harvest stage) is then subtracted from the calculated volume to calculate the volume of red blood cells remaining in the processing chamber 52. In another embodiment, the red blood cell recovery stage may continue until the optical sensor 34 detects a non-red blood cell fluid (e.g., air) flowing through line L4.

Figure 14:
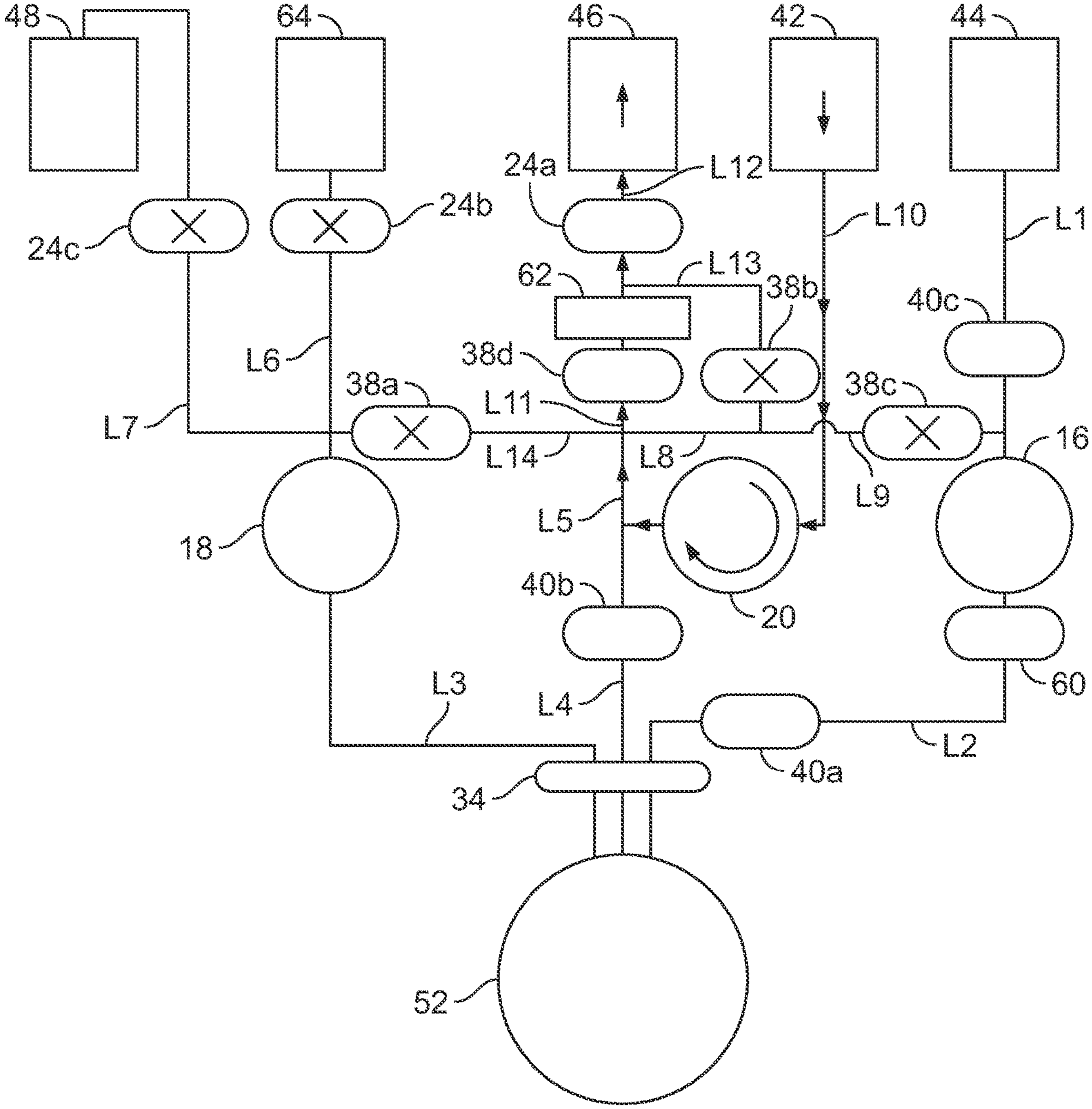
FIG. 14 is a schematic view of the blood processing system of FIG. 3 executing an “additive solution flush” stage of an exemplary blood processing procedure, with additive solution being directed through a leukoreduction filter before entering a red blood cell collection container.
Figure 15:
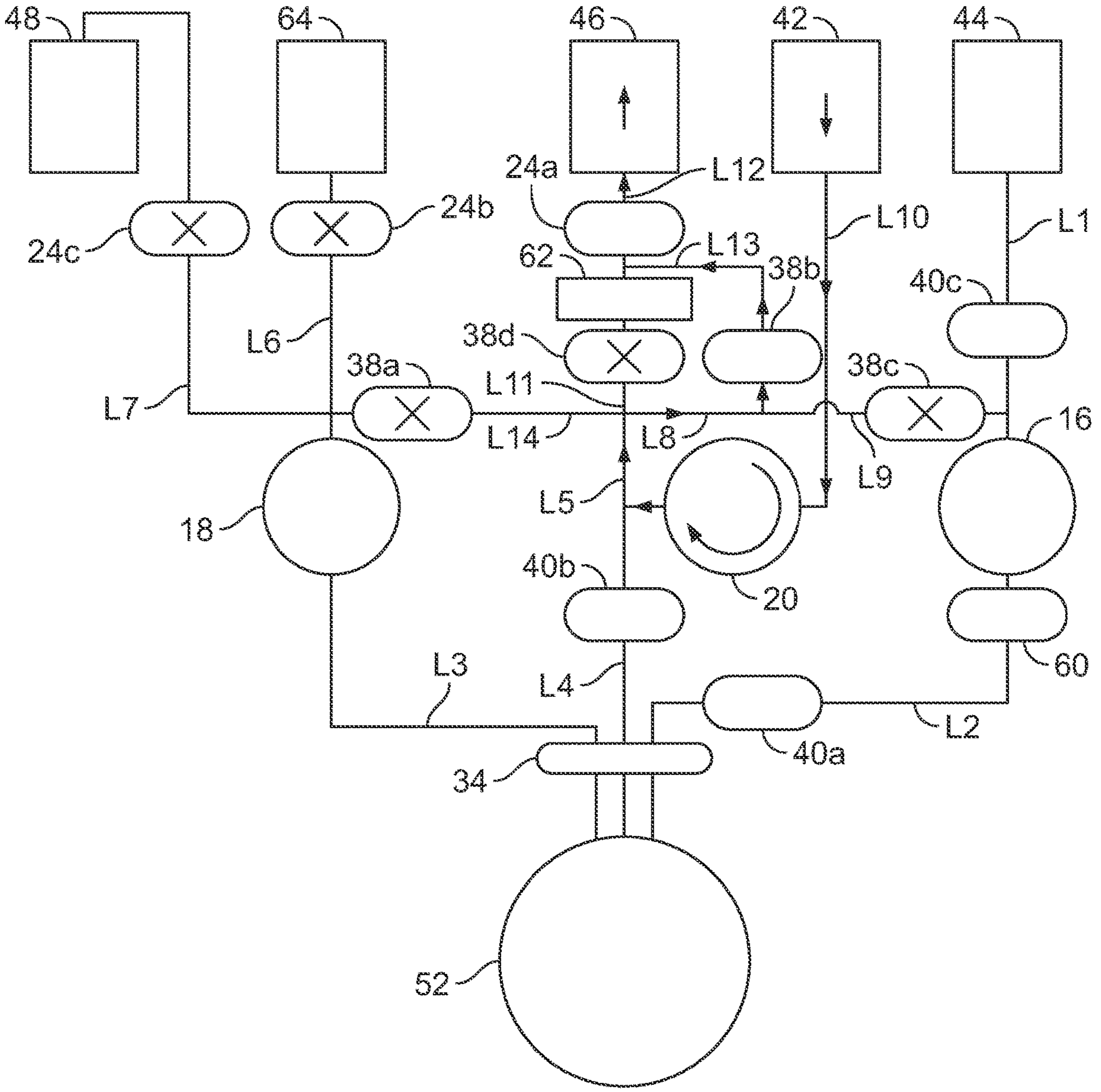
FIG. 15 is a schematic view of a variation of the “additive solution flush” stage of FIG. 14 in which the additive solution enters the red blood cell collection container without passing through the leukoreduction filter.

Once the red blood cell recovery stage is complete, the procedure will transition to an "additive solution flush" stage, with two variations being shown in FIGS. 14 and 15. During the additive solution flush stage, additive solution from the additive solution container 42 is conveyed into the red blood cell collection container 46 until a target amount of additive solution is in the red blood cell collection container 46. The only change in transitioning from the red blood cell recovery stage to the additive solution flush stage involves deactivating the plasma pump 18 to prevent plasma from being removed from the plasma collection container 48 (though it is also possible for the additive pump 20 to operate at a different rate). Thus, if the valve system was arranged to direct flow through the leukoreduction filter 62 at the end of the red blood cell recovery stage (as in FIG. 12), the additive solution flush stage will proceed as shown in FIG. 14. On the other hand, if the valve system was arranged to bypass the leukoreduction filter 62 at the end of the red blood cell recovery stage (as in FIG. 13), the additive solution flush stage will proceed as shown in FIG. 15. If the additive solution is pumped through the leukoreduction filter 62 during the additive solution flush stage (as in FIG. 14), the additive solution flowing through line L11 will flush residual red blood cells in the leukoreduction filter 62 into the red blood cell collection container 46 (in addition to achieving a proper additive solution volume for the red blood cell product). However, it is also within the scope of the present disclosure for valve 38*b* to be closed and valve 38*d* to be open at the end of the red blood cell recovery stage (as in FIG. 12), with valve 38*b* being open and valve 38*d* being closed at the beginning of the additive solution flush stage (as in FIG. 15), if the controller determines that it is advisable to begin bypassing the leukoreduction filter 62. Additionally, it is within the scope of the present disclosure for the valve system to be arranged as in FIG. 14 at the beginning of the additive solution flush stage (to direct additive solution through the leukoreduction filter 62) and to transition into the configuration of FIG. 15 before the end of the additive solution flush stage (to cause the additive solution to bypass the leukoreduction filter 62).

The additive solution flush stage will continue until a target amount of additive solution has been added to the red blood cell collection container 46. In one exemplary embodiment, the weight of the additive solution container 42 may be monitored by a weight scale, with a particular change in weight corresponding to the target amount of additive solution having been conveyed to the red blood cell collection container 46. Alternatively (or additionally), the weight of the red blood cell collection container 46 may be monitored by a weight scale, with a particular change in weight corresponding to the target amount of additive solution having been conveyed to the red blood cell collection container 46.

Figure 16:
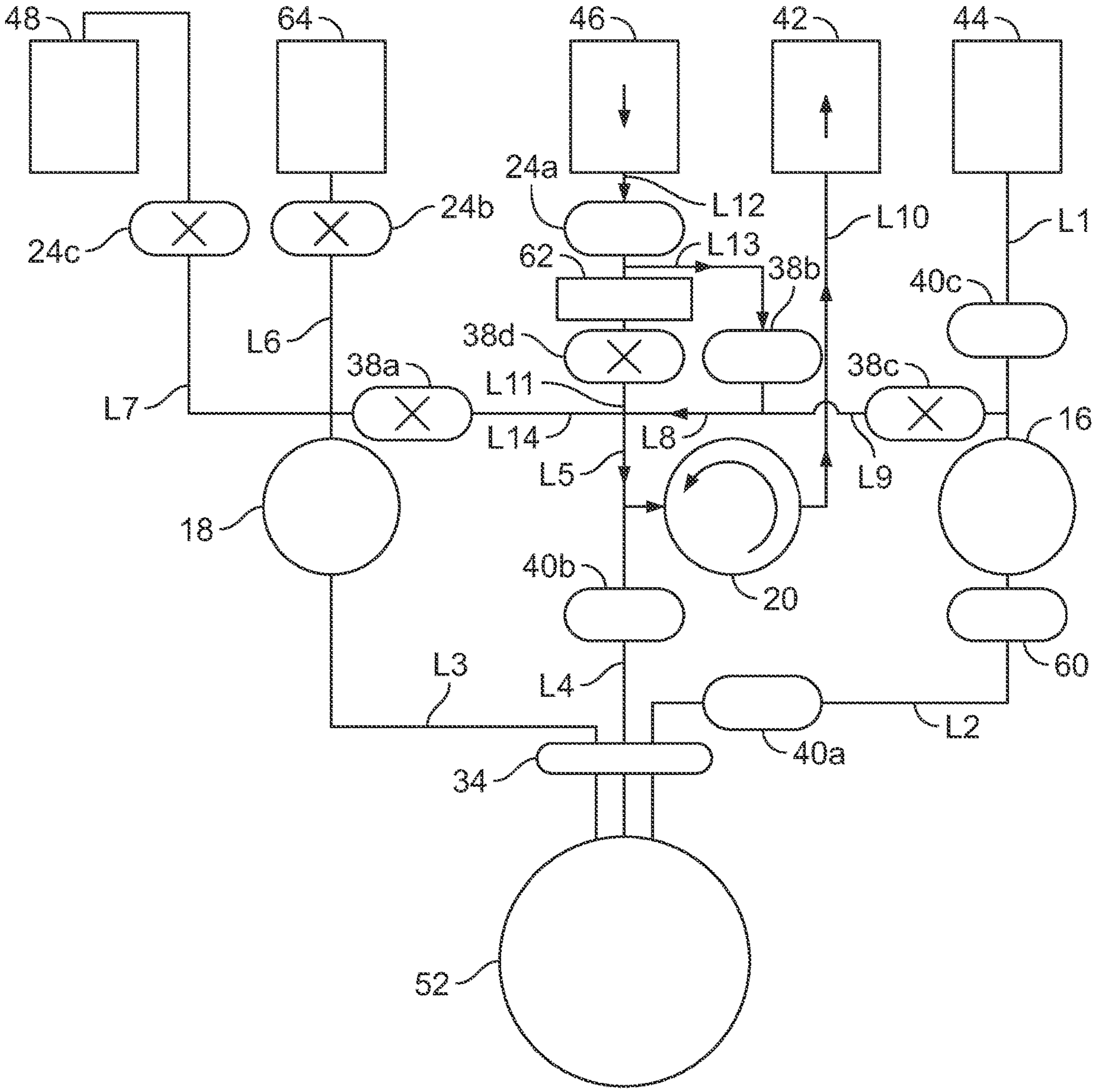
FIG. 16 is a schematic view of the blood processing system of FIG. 3 executing an "air evacuation" stage of an exemplary blood processing procedure.

When the additive solution flush stage is complete, the system will transition to an "air evacuation" stage, as shown in FIG. 16. During the air evacuation stage, the red blood cell collection container 46 is "burped" to remove all residual air for storage (just as air was removed from the plasma collection container 48 during the red blood cell recovery stage). This is done by reversing the direction of operation of the additive pump 20, closing valve 38*d* (if not already closed at the end of the additive solution flush stage), and opening valve 38*b* (if not already open at the end of the additive solution flush stage). The additive pump 20 draws air out of the red blood cell collection container 46, through line L12 and open clamp 24*a,* into line L13 and through open valve 38*b*. The air continues through line L8, line L5, and line L10, with the air ending up in the additive solution container 42. While FIG. 16 shows the air being evacuated from the red blood cell collection container 46 to the additive solution container 42, it is within the scope of the present disclosure for all or a portion of the air to be directed to a different location of the fluid flow circuit 12 (e.g., into the processing chamber 52 and/or into the whole blood container 44, if provided).

The air evacuation stage will continue until all of the air is removed from the red blood cell collection container 46, which may be determined (for example) by detecting a change in the weight of the red blood cell collection container 46 (e.g., using a weight scale).

Figure 17:
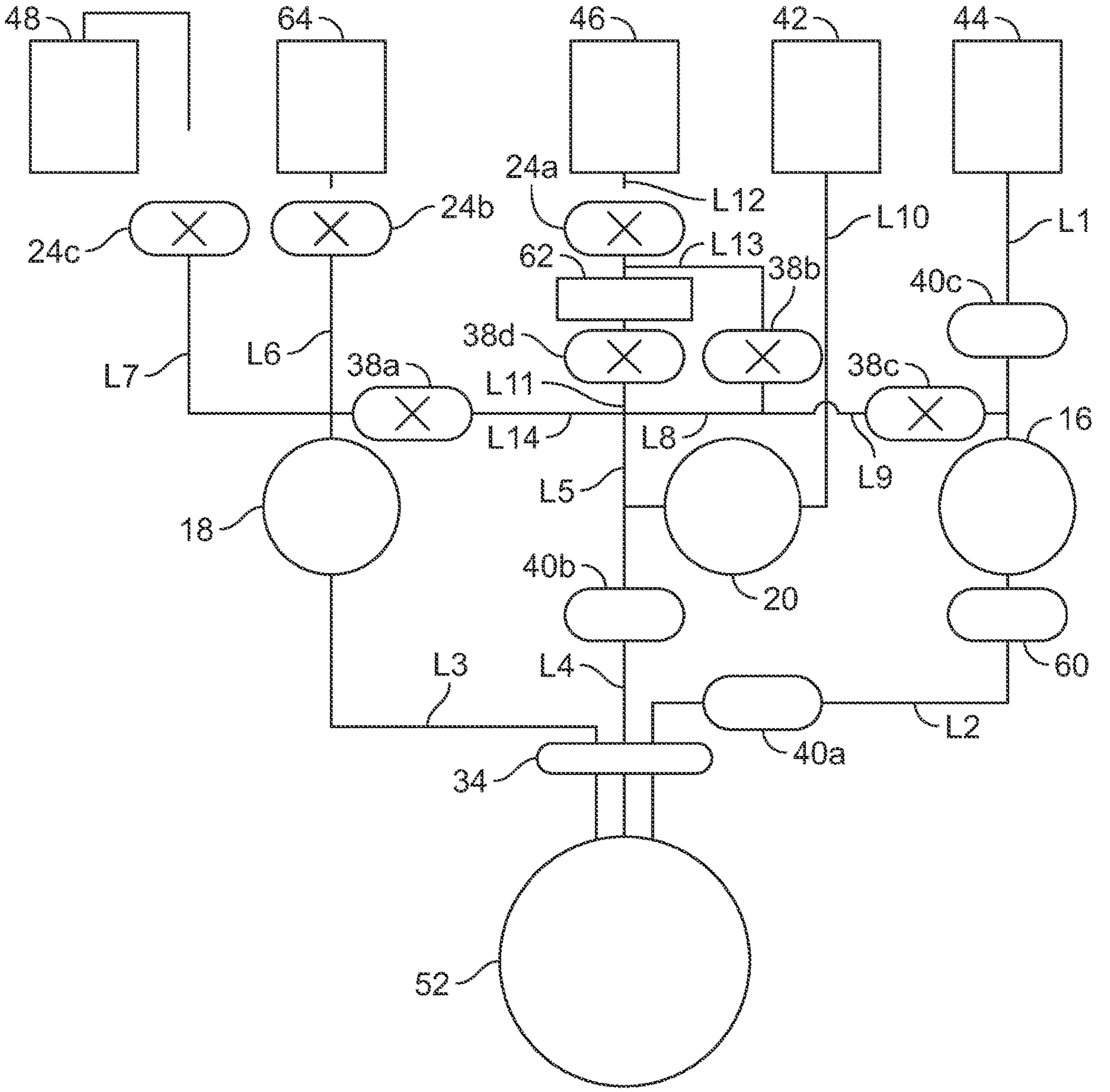
FIG. 17 is a schematic view of the blood processing system of FIG. 3 executing a "sealing" stage of an exemplary blood processing procedure.

Upon completion of the air evacuation stage, any of a number of post-processing stages may be executed. For example, FIG. 17 shows a "sealing" stage in which all of the clamps and valves are closed and all of the pumps are deactivated. The line L12 connected to the red blood cell collection container 46, the line L7 connected to the plasma collection container 48, and the line L6 connected to the platelet concentrate collection container 64 are sealed and optionally severed for storage of the plasma, red blood cell, and platelet concentrate products. If lines L6, L7, and L12 are severed, the plasma collection container 48, the platelet concentrate collection container 64, and the red blood cell collection container 46 may be stored, while the remainder of the fluid flow circuit 12 is disposed of. Lines L6, L7, and L12 may be sealed (and optionally severed) according to any suitable approach, which may include being sealed by RF sealers incorporated or associated with clamps 24*a,* 24*b,* and 24*c,* for example. In another embodiment, the fluid flow circuit 12 may be removed from the processing device 10, with lines L6, L7, and L12 being sealed (and optionally severed) using a dedicated sealing device.

Aspects

Aspect 1. A blood processing system, comprising: a reusable processing device including a pump system, a valve system, a centrifuge, and a controller; and a disposable fluid flow circuit including a processing chamber received by the centrifuge, a red blood cell collection container, a platelet concentrate collection container, and a plurality of conduits fluidly connecting the components of the fluid flow circuit, wherein the controller is configured to command the pump system and the valve system to cooperate to convey whole blood from a blood source to the processing chamber; execute an establish separation stage in which the centrifuge operates to separate the whole blood in the processing chamber into plasma and red blood cells and the pump system and the valve system cooperate to convey separated plasma and red blood cells out of the processing chamber, recombine the separated plasma and red blood cells as recombined whole blood, and convey the recombined whole blood into the processing chamber; execute a collection stage in which the pump system conveys the whole blood from the blood source to the processing chamber; the centrifuge separates the whole blood in the processing chamber into plasma, a buffy coat, and red blood cells; and the pump system and the valve system cooperate to convey at least a portion of the separated plasma out of the processing chamber and to convey at least a portion of the separated red blood cells out of the processing chamber and into the red blood cell collection container, with a fluid including the buffy coat remaining in the processing chamber; execute a platelet resuspension stage comprising a first phase in which the centrifuge is deactivated and the pump system and the valve system cooperate to circulate the fluid in the processing chamber through the fluid flow circuit to form a homogenous mixture, and a second phase in which the centrifuge operates to separate the homogenous mixture into a platelet concentrate and red blood cells; and execute a platelet harvest stage in which the pump system and the valve system cooperate to convey whole blood from the blood source or at least a portion of the contents of the red blood cell collection container into the processing chamber to convey at least a portion of the platelet concentrate out of the processing chamber and into the platelet concentrate collection container.

Aspect 2. The blood processing system of Aspect 1, wherein the fluid flow circuit includes a whole blood container containing one unit of whole blood, and the blood source is the whole blood container.

Aspect 3. The blood processing system of Aspect 2, wherein the processing device includes a first pressure sensor configured to measure hydrostatic pressure of the whole blood container, and the controller is configured to end the collection stage based at least in part on the hydrostatic pressure of the whole blood container.

Aspect 4. The blood processing system of any one of Aspects 2-3, wherein the processing device includes a first weight scale configured to measure a weight of the whole blood container, and the controller is configured to end the collection stage based at least in part on the weight of the whole blood container.

Aspect 5. The blood processing system of Aspect 1, wherein the blood source is a living donor.

Aspect 6. The blood processing system of any one of the preceding Aspects, wherein the processing device includes an interface detector configured to determine a location of an interface between separated blood components within the processing chamber, and the controller is configured to end the establish separation stage when the interface detector has determined that the interface is at a target location and when the controller has determined that steady state separation has been achieved.

Aspect 7. The blood processing system of any one of the preceding Aspects, wherein the processing device includes a leukoreduction filter, and the pump system and the valve system cooperate to convey said at least a portion of the separated red blood cells through the leukoreduction filter before being conveyed into the red blood cell collection container during at least a portion of the collection stage.

Aspect 8. The blood processing system of Aspect 7, wherein the processing device includes a second pressure sensor configured to measure pressure of the leukoreduction filter, and the controller is configured to control the valve system to direct said at least a portion of the separated red blood cells to the red blood cell collection container without first passing through the leukoreduction filter based at least in part on the pressure of the leukoreduction filter.

Aspect 9. The blood processing system of any one of the preceding Aspects, wherein the processing device includes an optical sensor configured to monitor fluid exiting the processing chamber, and the controller is configured to end the platelet harvest stage when the optical sensor detects a non-platelet concentrate fluid exiting the processing chamber.

Aspect 10. The blood processing system of any one of the preceding Aspects, wherein during the platelet harvest stage, the pump system and the valve system cooperate to convey whole blood from the blood source into the processing chamber and the centrifuge operates to separate the whole blood in the processing chamber into platelet-rich plasma and red blood cells, with the platelet-rich plasma forcing said at least a portion of the platelet concentrate from the processing chamber and into the platelet concentrate collection container.

Aspect 11. The blood processing system of any one of Aspects 1-9, wherein during the platelet harvest stage, the pump system and the valve system cooperate to convey said at least a portion of the contents of the red blood cell container into the processing chamber to force said at least a portion of the platelet concentrate from the processing chamber and into the platelet concentrate collection container.

Aspect 12. The blood processing system of any one of the preceding Aspects, wherein the controller is further configured to execute a blood prime stage in which the pump system conveys whole blood from the blood source to the processing chamber to convey air within the fluid flow circuit into a plasma collection container of the fluid flow circuit.

Aspect 13. The blood processing system of Aspect 12, wherein the controller is further configured to execute a red blood cell recovery stage in which the pump system and the valve system cooperate to convey air from the plasma collection container into the processing chamber to convey separated red blood cells out of the processing chamber and into the red blood cell collection container.

Aspect 14. The blood processing system of any one of the preceding Aspects, wherein the fluid flow circuit includes an additive solution container, and the pump system and the valve system cooperate to convey additive solution out of the additive solution container to combine with separated red blood cells being conveyed into the red blood cell collection container.

Aspect 15. The blood processing system of Aspect 14, wherein the controller is further configured to execute an additive solution flush stage after the platelet harvest stage in which the pump system and the valve system cooperate to convey additive solution from the additive solution container to the red blood cell collection container until a target amount of additive solution has been conveyed into the red blood cell collection container.

Aspect 16. The blood processing system of any one of the preceding Aspects, wherein the controller is further configured to execute an air evacuation stage after the platelet harvest stage in which the pump system and the valve system cooperate to convey air out of the red blood cell collection container.

Aspect 17. The blood processing system of any one of the preceding Aspects, wherein the processing device includes a sealing system, and the controller is configured to control the sealing system to seal a first conduit connected to the red blood cell collection container and to seal a second conduit connected to the platelet concentrate collection container after the platelet harvest stage.

Aspect 18. The blood processing system of any one of the preceding Aspects, wherein the centrifuge operates at a slower speed during the second phase of the platelet resuspension phase than during the collection phase.

Aspect 19. The blood processing system of any one of the preceding Aspects, wherein the processing device includes an optical sensor configured to monitor fluid exiting the processing chamber, and the controller is configured to end the first phase of the platelet resuspension stage when the optical sensor detects the homogeneous mixture exiting the processing chamber.

Aspect 20. The blood processing system of any one of the preceding Aspects, wherein the processing device includes an optical sensor configured to monitor fluid exiting the processing chamber, and the controller is configured to end the second phase of the platelet resuspension stage when the optical sensor detects platelet concentrate having a target platelet content exiting the processing chamber.

Aspect 21. A method for processing whole blood into a red blood cell product, a plasma product, and a platelet product, comprising: conveying whole blood from a blood source to a processing chamber of a fluid flow circuit; executing an establish separation stage in which a centrifuge is operated to separate the whole blood in the processing chamber into plasma and red blood cells, separated plasma and red blood cells are conveyed out of the processing chamber and recombined as recombined whole blood, and the recombined whole blood is conveyed into the processing chamber; executing a collection stage in which whole blood is conveyed from the blood source to the processing chamber; the centrifuge is operated to separate the whole blood in the processing chamber into plasma, a buffy coat, and red blood cells; at least a portion of the separated plasma is conveyed out of the processing chamber; and at least a portion of the separated red blood cells is conveyed out of the processing chamber and into a red blood cell collection container of the fluid flow circuit, with a fluid including the buffy coat remaining in the processing chamber; executing a platelet resuspension stage comprising a first phase in which the centrifuge is deactivated and the fluid in the processing chamber is recirculated through the fluid flow circuit to form a homogenous mixture, and a second phase in which the centrifuge is operated to separate the homogenous mixture into a platelet concentrate and red blood cells; and executing a platelet harvest stage in which whole blood from the blood source or at least a portion of the contents of the red blood cell collection container is conveyed into the processing chamber to convey at least a portion of the platelet concentrate out of the processing chamber and into a platelet concentrate collection container of the fluid flow circuit.

Aspect 22. The method of Aspect 21, wherein the platelet harvest stage includes conveying whole blood from the blood source into the processing chamber and operating the centrifuge to separate the whole blood in the processing chamber into platelet-rich plasma and red blood cells, with the platelet-rich plasma forcing said at least a portion of the platelet concentrate from the processing chamber and into the platelet concentrate collection container.

Aspect 23. The method of Aspect 21, wherein the platelet harvest stage includes conveying said at least a portion of the contents of the red blood cell container into the processing chamber to force said at least a portion of the platelet concentrate from the processing chamber and into the platelet concentrate collection container.

Aspect 24. The method of any one of Aspects 21-23, wherein the fluid flow circuit includes a whole blood container containing one unit of whole blood, and the blood source is the whole blood container.

Aspect 25. The method of Aspect 24, wherein said executing the collection stage includes measuring hydrostatic pressure of the whole blood container, and ending the collection stage based at least in part on the hydrostatic pressure of the whole blood container.

Aspect 26. The method of any one of Aspects 24-25, wherein said executing the collection stage includes measuring a weight of the whole blood container, and ending the collection stage based at least in part on the weight of the whole blood container.

Aspect 27. The method of any one Aspects 21-23, wherein the blood source is a living donor.

Aspect 28. The method of any one of Aspects 21-27, wherein said executing the establish separation stage includes determining a location of an interface between separated blood components within the processing chamber, and ending the establish separation stage when it has been determined that the interface is at a target location and that steady state separation has been achieved.

Aspect 29. The method of any one of Aspects 21-28, wherein said executing the collection stage includes conveying said at least a portion of the separated red blood cells through a leukoreduction filter before conveying said at least a portion of the separated red blood cells into the red blood cell collection container during at least a portion of the collection stage.

Aspect 30. The method of Aspect 29, wherein said executing the collection stage includes measuring pressure of the leukoreduction filter, and directing said at least a portion of the separated red blood cells to the red blood cell collection container without first passing through the leukoreduction filter based at least in part on the pressure of the leukoreduction filter.

Aspect 31. The method of any one of Aspects 21-30, wherein said executing the platelet harvest stage includes monitoring fluid exiting the processing chamber, and ending the platelet harvest stage when a non-platelet concentrate fluid is detected exiting the processing chamber.

Aspect 32. The method of any one of Aspects 21-31, further comprising executing a blood prime stage in which whole blood is conveyed from the blood source to the processing chamber of the fluid flow circuit to convey air within the fluid flow circuit into a plasma collection container of the fluid flow circuit.

Aspect 33. The method of Aspect 32, further comprising executing a red blood cell recovery stage in which air from the plasma collection container is conveyed into the processing chamber to convey separated red blood cells out of the processing chamber to convey separated red blood cells out of the processing chamber and into the red blood cell collection container.

Aspect 34. The method of any one of Aspects 21-33, further comprising conveying additive solution out of an additive solution container of the fluid flow circuit to combine with separated red blood cells being conveyed into the red blood cell collection container.

Aspect 35. The method of Aspect 34, further comprising executing an additive solution flush stage in which additive solution is conveyed from the additive solution container to the red blood cell collection container until a target amount of additive solution has been conveyed into the red blood cell collection container.

Aspect 36. The method of any one of Aspects 21-35, further comprising executing an air evacuation stage in which air is conveyed out of the red blood cell collection container.

Aspect 37. The method of any one of Aspects 21-36, further comprising sealing a first conduit connected to the red blood cell collection container and sealing a second conduit connected to the platelet concentrate collection container after the platelet harvest stage.

Aspect 38. The method of any one of Aspects 21-37, wherein said executing the platelet resuspension stage includes operating the centrifuge at a slower speed during the second phase of the platelet resuspension phase than during the collection phase.

Aspect 39. The method of any one of Aspects 21-38, further comprising monitoring fluid exiting the processing chamber, and ending the first phase of the platelet resuspension stage when the homogeneous mixture is detected exiting the processing chamber.

Aspect 40. The method of any one of Aspects 21-39, further comprising monitoring fluid exiting the processing chamber, and ending the second phase of the platelet resuspension stage when platelet concentrate having a target platelet content is detected exiting the processing chamber.

Aspect 41. A blood processing device, comprising: a pump system; a valve system; a centrifuge; and a controller configured to command the pump system and the valve system to cooperate to convey whole blood from a blood source into the centrifuge, execute an establish separation stage in which the centrifuge operates to separate the whole blood in the centrifuge into plasma and red blood cells and the pump system and the valve system cooperate to convey separated plasma and red blood cells out of the centrifuge, recombine the separated plasma and red blood cells as recombined whole blood, and convey the recombined whole blood into the centrifuge; execute a collection stage in which the pump system conveys the whole blood from the blood source to the centrifuge; the centrifuge separates the whole blood in the centrifuge into plasma, a buffy coat, and red blood cells; and the pump system and the valve system cooperate to convey at least a portion of the separated plasma out of the centrifuge and to convey at least a portion of the separated red blood cells out of the centrifuge for collection, with a fluid including the buffy coat remaining in the centrifuge; execute a platelet resuspension stage comprising a first phase in which the centrifuge is deactivated and the pump system and the valve system cooperate to circulate the fluid in the centrifuge through the centrifuge to form a homogenous mixture, and a second phase in which the centrifuge operates to separate the homogenous mixture into a platelet concentrate and red blood cells; and execute a platelet harvest stage in which the pump system and the valve system cooperate to convey whole blood from the blood source or at least a portion of the collected red blood cells into the centrifuge to convey at least a portion of the platelet concentrate out of the centrifuge for collection.

Aspect 42. The blood processing device of Aspect 41, wherein the blood source is a whole blood container.

Aspect 43. The blood processing device of Aspect 42, further comprising a first pressure sensor configured to measure hydrostatic pressure of the whole blood container, wherein the controller is configured to end the collection stage based at least in part on the hydrostatic pressure of the whole blood container.

Aspect 44. The blood processing device of any one of Aspects 42-43, further comprising a first weight scale configured to measure a weight of the whole blood container, wherein the controller is configured to end the collection stage based at least in part on the weight of the whole blood container.

Aspect 45. The blood processing device of Aspect 41, wherein the blood source is a living donor.

Aspect 46. The blood processing device of any one of Aspects 41-45, further comprising an interface detector configured to determine a location of an interface between separated blood components within the centrifuge, wherein the controller is configured to end the establish separation stage when the interface detector has determined that the interface is at a target location and when the controller has determined that steady state separation has been achieved.

Aspect 47. The blood processing device of any one of Aspects 41-46, wherein the controller is configured to command the pump system and the valve system to cooperate to convey said at least a portion of the separated red blood cells through a leukoreduction filter after being conveyed from the centrifuge during at least a portion of the collection stage.

Aspect 48. The blood processing device of Aspect 47, further comprising a second pressure sensor configured to measure pressure of the leukoreduction filter, wherein the controller is configured to control the valve system to direct said at least a portion of the separated red blood cells from the centrifuge without first passing through the leukoreduction filter based at least in part on the pressure of the leukoreduction filter.

Aspect 49. The blood processing device of any one of Aspects 41-48, further comprising an optical sensor configured to monitor fluid exiting the centrifuge, wherein the controller is configured to end the platelet harvest stage when the optical sensor detects a non-platelet concentrate fluid exiting the centrifuge.

Aspect 50. The blood processing device of any one of Aspects 41-49, wherein during the platelet harvest stage, the pump system and the valve system cooperate to convey whole blood from the blood source into the centrifuge which operates to separate the whole blood into platelet-rich plasma and red blood cells, with the platelet-rich plasma forcing said at least a portion of the platelet concentrate from the centrifuge for collection.

Aspect 51. The blood processing device of any one of Aspects 41-49, wherein during the platelet harvest stage, the pump system and the valve system cooperate to convey said at least a portion of the collected red blood cells into the centrifuge to force said at least a portion of the platelet concentrate from the centrifuge for collection.

Aspect 52. The blood processing device of any one of Aspects 41-51, wherein the controller is further configured to execute a blood prime stage in which the pump system conveys whole blood from the blood source to the centrifuge to convey air out of the centrifuge.

Aspect 53. The blood processing device of Aspect 52, wherein the controller is further configured to execute a red blood cell recovery stage in which the pump system and the valve system cooperate to convey air into the centrifuge to convey separated red blood cells out of the centrifuge for collection.

Aspect 54. The blood processing device of any one of Aspects 41-53, wherein the pump system and the valve system cooperate to convey additive solution to combine with separated red blood cells being conveyed out of the centrifuge.

Aspect 55. The blood processing device of Aspect 54, wherein the controller is further configured to execute an additive solution flush stage after the platelet harvest stage in which the pump system and the valve system cooperate to convey additive solution to combine with the collected red blood cells until a target amount of additive solution has been added to the collected red blood cells.

Aspect 56. The blood processing device of any of Aspects 41-55, wherein the controller is further configured to execute an air evacuation stage after the platelet harvest stage in which the pump system and the valve system cooperate to convey air away from the collected red blood cells.

Aspect 57. The blood processing device of any of Aspects 41-56, further comprising a sealing system, wherein the controller is configured to control the sealing system to seal a first conduit connected to a red blood cell collection container and to seal a second conduit connected to a platelet concentrate collection container after the platelet harvest stage.

Aspect 58. The blood processing device of any one of Aspects 41-57, wherein the centrifuge operates at a slower speed during the second phase of the platelet resuspension phase than during the collection phase.

Aspect 59. The blood processing device of any one of Aspects 41-58, further comprising an optical sensor configured to monitor fluid exiting the centrifuge, wherein the controller is configured to end the first phase of the platelet resuspension stage when the optical sensor detects the homogeneous mixture exiting the centrifuge.

Aspect 60. The blood processing device of any one of Aspects 41-59, further comprising an optical sensor configured to monitor fluid exiting the centrifuge, wherein the controller is configured to end the second phase of the platelet resuspension stage when the optical sensor detects platelet concentrate having a target platelet content exiting the centrifuge.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:

a reusable processing device including a pump system, a valve system, a centrifuge, and a controller; and a disposable fluid flow circuit including
a processing chamber received by the centrifuge,
a red blood cell collection container,
a platelet concentrate collection container, and
a plurality of conduits fluidly connecting the components of the fluid flow circuit, wherein the controller is configured to
command the pump system and the valve system to cooperate to convey whole blood from a blood source to the processing chamber;
execute an establish separation stage in which the centrifuge operates to separate the whole blood in the processing chamber into plasma and red blood cells and the pump system and the valve system cooperate to convey separated plasma and red blood cells out of the processing chamber, recombine the separated plasma and red blood cells as recombined whole blood, and convey the recombined whole blood into the processing chamber;
execute a collection stage in which the pump system conveys the whole blood from the blood source to the processing chamber; the centrifuge separates the whole blood in the processing chamber into plasma, a buffy coat, and red blood cells; and the pump system and the valve system cooperate to convey at least a portion of the separated plasma out of the processing chamber and to convey at least a portion of the separated red blood cells out of the processing chamber and into the red blood cell collection container, with a fluid including the buffy coat remaining in the processing chamber;
execute a platelet resuspension stage comprising a first phase in which the centrifuge is deactivated and the pump system and the valve system cooperate to circulate the fluid in the processing chamber through the fluid flow circuit to form a homogenous mixture, and a second phase in which the centrifuge operates to separate the homogenous mixture into a platelet concentrate and red blood cells; and
execute a platelet harvest stage in which the pump system and the valve system cooperate to convey whole blood from the blood source or at least a portion of the contents of the red blood cell collection container into the processing chamber to convey at least a portion of the platelet concentrate out of the processing chamber and into the platelet concentrate collection container.

2. A method for processing whole blood into a red blood cell product, a plasma product, and a platelet product, comprising:
conveying whole blood from a blood source to a processing chamber of a fluid flow circuit;
executing an establish separation stage in which a centrifuge is operated to separate the whole blood in the processing chamber into plasma and red blood cells, separated plasma and red blood cells are conveyed out of the processing chamber and recombined as recombined whole blood, and the recombined whole blood is conveyed into the processing chamber;
executing a collection stage in which whole blood is conveyed from the blood source to the processing chamber; the centrifuge is operated to separate the whole blood in the processing chamber into plasma, a buffy coat, and red blood cells; at least a portion of the separated plasma is conveyed out of the processing chamber; and at least a portion of the separated red blood cells is conveyed out of the processing chamber and into a red blood cell collection container of the fluid flow circuit, with a fluid including the buffy coat remaining in the processing chamber;
executing a platelet resuspension stage comprising a first phase in which the centrifuge is deactivated and the fluid in the processing chamber is recirculated through the fluid flow circuit to form a homogenous mixture, and a second phase in which the centrifuge is operated to separate the homogenous mixture into a platelet concentrate and red blood cells; and
executing a platelet harvest stage in which whole blood from the blood source or at least a portion of the contents of the red blood cell collection container is conveyed into the processing chamber to convey at least a portion of the platelet concentrate out of the processing chamber and into a platelet concentrate collection container of the fluid flow circuit.

3. A blood processing device, comprising:
a pump system;
a valve system;
a centrifuge; and
a controller configured to
command the pump system and the valve system to cooperate to convey whole blood from a blood source into the centrifuge,
execute an establish separation stage in which the centrifuge operates to separate the whole blood in the centrifuge into plasma and red blood cells and the pump system and the valve system cooperate to convey separated plasma and red blood cells out of the centrifuge, recombine the separated plasma and red blood cells as recombined whole blood, and convey the recombined whole blood into the centrifuge;
execute a collection stage in which the pump system conveys the whole blood from the blood source to the centrifuge; the centrifuge separates the whole blood in the centrifuge into plasma, a buffy coat, and red blood cells; and the pump system and the valve system cooperate to convey at least a portion of the separated plasma out of the centrifuge and to convey at least a portion of the separated red blood cells out of the centrifuge for collection, with a fluid including the buffy coat remaining in the centrifuge;
execute a platelet resuspension stage comprising a first phase in which the centrifuge is deactivated and the pump system and the valve system cooperate to circulate the fluid in the centrifuge through the centrifuge to form a homogenous mixture, and a second phase in which the centrifuge operates to separate the homogenous mixture into a platelet concentrate and red blood cells; and
execute a platelet harvest stage in which the pump system and the valve system cooperate to convey whole blood from the blood source or at least a portion of the collected red blood cells into the centrifuge to convey at least a portion of the platelet concentrate out of the centrifuge for collection.

4. The blood processing device of claim 3, wherein the blood source is a whole blood container.

5. The blood processing device of claim 4, further comprising a first pressure sensor configured to measure hydrostatic pressure of the whole blood container, wherein the controller is configured to end the collection stage based at least in part on the hydrostatic pressure of the whole blood container.

6. The blood processing device of claim 4, further comprising a first weight scale configured to measure a weight of the whole blood container, wherein the controller is configured to end the collection stage based at least in part on the weight of the whole blood container.

7. The blood processing device of claim 3, wherein the blood source is a living donor.

8. The blood processing device of claim 3, further comprising an interface detector configured to determine a location of an interface between separated blood components within the centrifuge, wherein the controller is configured to end the establish separation stage when the interface detector has determined that the interface is at a target location and when the controller has determined that steady state separation has been achieved.

9. The blood processing device of claim 3, wherein the controller is configured to command the pump system and the valve system to cooperate to convey said at least a portion of the separated red blood cells through a leukoreduction filter after being conveyed from the centrifuge during at least a portion of the collection stage.

10. The blood processing device of claim 9, further comprising a second pressure sensor configured to measure pressure of the leukoreduction filter, wherein the controller is configured to control the valve system to direct said at least a portion of the separated red blood cells from the centrifuge without first passing through the leukoreduction filter based at least in part on the pressure of the leukoreduction filter.

11. The blood processing device of claim 3, further comprising an optical sensor configured to monitor fluid exiting the centrifuge, wherein the controller is configured to end the platelet harvest stage when the optical sensor detects a non-platelet concentrate fluid exiting the centrifuge.

12. The blood processing device of claim 3, wherein the controller is configured to command the pump system and the valve system during the platelet harvest stage to cooperate to convey whole blood from the blood source into the centrifuge and to command the centrifuge during the platelet harvest stage to separate the whole blood into platelet-rich plasma and red blood cells so as to cause the platelet-rich plasma to force said at least a portion of the platelet concentrate from the centrifuge for collection.

13. The blood processing device of claim 3, wherein the controller is configured to command the pump system and the valve system during the platelet harvest stage to cooperate to convey said at least a portion of the collected red blood cells into the centrifuge to force said at least a portion of the platelet concentrate from the centrifuge for collection.

14. The blood processing device of claim 3, wherein the controller is further configured to execute a blood prime stage in which the pump system conveys whole blood from the blood source to the centrifuge to convey air out of the centrifuge.

15. The blood processing device of claim 14, wherein the controller is further configured to execute a red blood cell recovery stage in which the pump system and the valve system cooperate to convey air into the centrifuge to convey separated red blood cells out of the centrifuge for collection.

16. The blood processing device of claim 3, wherein the controller is configured to command the pump system and the valve system to cooperate to convey additive solution to combine with separated red blood cells being conveyed out of the centrifuge.

17. The blood processing device of claim 16, wherein the controller is further configured to execute an additive solution flush stage after the platelet harvest stage in which the controller commands the pump system and the valve system to cooperate to convey additive solution to combine with the collected red blood cells until a target amount of additive solution has been added to the collected red blood cells.

18. The blood processing device of claim 3, wherein the controller is further configured to execute an air evacuation stage after the platelet harvest stage in which the pump system and the valve system cooperate to convey air away from the collected red blood cells.

19. The blood processing device of claim 3, further comprising a sealing system, wherein the controller is configured to control the sealing system to seal a first conduit connected to a red blood cell collection container and to seal a second conduit connected to a platelet concentrate collection container after the platelet harvest stage.

20. The blood processing device of claim 3, wherein the centrifuge operates at a slower speed during the second phase of the platelet resuspension phase than during the collection phase.

21. The blood processing device of claim 3, further comprising an optical sensor configured to monitor fluid exiting the centrifuge, wherein the controller is configured to end the first phase of the platelet resuspension stage when the optical sensor detects the homogeneous mixture exiting the centrifuge.

22. The blood processing device of claim 3, further comprising an optical sensor configured to monitor fluid exiting the centrifuge, wherein the controller is configured to end the second phase of the platelet resuspension stage when the optical sensor detects platelet concentrate having a target platelet content exiting the centrifuge.

* * * * *